(12) United States Patent
Debinski et al.

(10) Patent No.: US 10,676,529 B2
(45) Date of Patent: Jun. 9, 2020

(54) ANTIBODIES AGAINST HUMAN AND CANINE IL-13RA2

(71) Applicant: Wake Forest University Health Sciences, Winston-Salem, NC (US)

(72) Inventors: Waldemar Debinski, Winston-Salem, NC (US); Denise Mazess Herpai, Winston-Salem, NC (US)

(73) Assignee: Wake Forest University Health Sciences, Winston-Salem, NC (US)

( * ) Notice: Subject to any disclaimer, the term of this patent is extended or adjusted under 35 U.S.C. 154(b) by 0 days.

(21) Appl. No.: 15/835,566

(22) Filed: Dec. 8, 2017

(65) Prior Publication Data

US 2018/0155437 A1    Jun. 7, 2018

Related U.S. Application Data

(62) Division of application No. 14/776,356, filed as application No. PCT/US2014/027254 on Mar. 14, 2014, now Pat. No. 9,868,788.

(60) Provisional application No. 61/788,312, filed on Mar. 15, 2013.

(51) Int. Cl.
| | |
|---|---|
| C07K 16/28 | (2006.01) |
| A61K 39/395 | (2006.01) |
| A61K 47/68 | (2017.01) |
| A61K 49/00 | (2006.01) |
| C12N 9/00 | (2006.01) |
| A61K 47/69 | (2017.01) |
| A61K 39/00 | (2006.01) |

(52) U.S. Cl.
CPC ...... *C07K 16/2866* (2013.01); *A61K 39/3955* (2013.01); *A61K 47/6813* (2017.08); *A61K 47/6829* (2017.08); *A61K 47/6849* (2017.08); *A61K 47/6851* (2017.08); *A61K 47/6911* (2017.08); *A61K 49/0004* (2013.01); *C12N 9/93* (2013.01); *A61K 2039/505* (2013.01); *C07K 2317/24* (2013.01); *C07K 2317/33* (2013.01); *C07K 2317/34* (2013.01); *C07K 2317/56* (2013.01); *C07K 2317/73* (2013.01); *C07K 2317/76* (2013.01); *C12Y 603/01004* (2013.01)

(58) Field of Classification Search
None
See application file for complete search history.

(56) References Cited

U.S. PATENT DOCUMENTS

| | | | |
|---|---|---|---|
| 6,703,360 B2 | 3/2004 | McCall et al. | |
| 8,362,207 B2 | 1/2013 | Debinski et al. | |
| 2002/0131954 A1 | 9/2002 | Tobinick | |
| 2006/0067920 A1 | 3/2006 | Jensen | |
| 2006/0099652 A1 | 5/2006 | Gately et al. | |
| 2009/0123371 A1 | 5/2009 | Debinski et al. | |
| 2011/0110955 A1 | 5/2011 | Debinski et al. | |
| 2011/0201029 A1 | 8/2011 | Caput et al. | |
| 2012/0052080 A1 | 3/2012 | Okada | |

FOREIGN PATENT DOCUMENTS

| | | |
|---|---|---|
| EP | 1293805 A2 | 3/2003 |
| WO | WO 01/77332 A | 10/2001 |
| WO | WO 2004/087758 A2 | 10/2004 |
| WO | WO 2008/146911 A1 | 12/2008 |

OTHER PUBLICATIONS

Balyasnikova et al, 2012, Manuscript M112.370015, pp. 1-32.*
Kioi et al, Technology in Cancer Research and Treatment, 2006, vol. 5, No. 3, pp. 239-250.*
Lloyd et al Protein Engineering, Design & Selection, 2009, vol. 22, No. 3, pp. 159-168.*
Edwards et al, Journal of Molecular Biology, 2003, vol. 334, pp. 103-118.*
Goel et al. (The Journal of Immunology 173(12):7358-7367.*
Burks et al. (PNAS 94:412-417 (1997).*
Brummell et al. (Biochemistry 32:1180-1187 (1993)).*
Kobayashi et al. (Protein Engineering 12:879-844 (1999).*
Takenouchei et al, (Clinical Cancer Research; 2011, 17(9); 2819-2829).*
Andrews A-L et at. IL-13 receptor (alpha) 2: A regulator of II-13 and IL-4 signal transduction in primary human fibroblasts. Journal of Allergy Clinical Immunology. 2006; 118: 858-865.
Casset F et al. A peptide mimetic of an anti-CD4 monoclonal antibody by rational design. Biochemical and Biophysical Research Communications. 2003: 307: 198-205.
Debinski W et al. A novel chimeric protein composed of interleukin 13 and Pseudomonas exotoxin is highly cytotoxic to human carcinoma cells expressing receptors for interleukin 13 and interleukin 4. The Journal of Biological Chemistry. Jul. 14, 1995; 270(28) 16775-16780.
Debinski W et at. Abstracts from the 2009 joint meeting of the Society for Neuro-Oncology (SNO) and the American Association of neurological surgeons, abstract #328, Oct. 22-24, 2009, New Orleans, LA.
Hamada H et al. (WO 200814691), translation, published on Apr. 20, 2010.
Paul WE. Fundamental Immunology, 3rd Edition, 1993, pp. 292-295. Raven Press, NY.
Debinski W et al. New Agents for Targeting of IL-13RA2 Expressed in Primary Human and Canine Brain Tumors. PLoS ONE. Oct. 16, 2013; 10(8): e77719, pp. 1-15.
"TYKBNFEU114-Alignment" Alignment of human IL-13RA2 and canine IL-13RA2. Retrieved or the Internet <http://blast.ncbi.nlm.nih.gov/Blast.cgi?CMD=Get&RID=TYKBNFEU114>.

(Continued)

*Primary Examiner* — Bridget E Bunner
(74) *Attorney, Agent, or Firm* — Myers Bigel, P.A.

(57) ABSTRACT

Provided herein are monoclonal antibodies that specifically bind IL-13RA2 with cross-reactivity in humans and canines. Also provided are methods of use of the antibodies in the treatment and monitoring of cancers.

30 Claims, 21 Drawing Sheets

Specification includes a Sequence Listing.

(56) References Cited

OTHER PUBLICATIONS

International Search Report and Written Opinion, PCT/US2014/027254, dated Jul. 11, 2014.
Gibo DM et al. Interleukin 13 receptor alpha 2 is widely overexpressed in human and canine primary brain tumors as detected by novel bi-species specific monoclonal antibodies. Poster resentation, SNO 2012 conference, Nov. 15, 2012. 1 p.
Gibo DM at al. Highly potent cytotoxin targeting IL-12Rα2 in canine and human GBM, Poster presentation, SNO 2012 conference. Nov. 15, 2012. 1 p.
Candolfi M at al. Intracranial glioblastoma models in preclinical neuro-oncology: neuropathelogical characterization and tumor progression, J Neurooncol Nov. 2007; 85(2): 133-148.
Dickinson PJ et al. Canine spontaneous glioma; a translational model system for convection-enhanced delivery. Neuro-Oncology. Sep. 2010; 12(9): 928-940.
Barderas R et al. High expression of IL-13 receptor α2 in colorectal cancer is associated with invasion, liver metastasis, and poor prognosis. Cancer Res. Jun. 1, 2012: 72(11): 2780-90. Abstract only.
Fujisawa T et al. IL-13 regulates cancer invasion and metastasis through IL-13Rα2 via ERK/AP-1 pathway in mouse model of human ovarian cancer. Int J Cancer. Jul. 16, 2012; 131(2): 344-45. Abstract only.
Zhang J-G et al. Identification, purification, and characterization of a soluble interleukin (IL)-13-binding protein. The Journal of Biological Chemistry. Apr. 4, 1997; 272(14): 9474-9480.
Nakashima H et al. A novel combination immunotherapy for cancer by IL-13Rα2-targeted DNA vaccine and immunotoxin in murine tumor models. The Journal of Immunology, Oct. 17, 2011; 187: 1-12.
GenBank Accession No. AF315592, "*Homo sapiens* Pumillo 1 (PUMH1) mRNA, complete cds", retrieved from the internet on Jun. 21, 2016 at http://www.ncbi.nlm.nih.gov, 3 pages.
GenBank Accession No. ABW24725, "Immunoglobulin gamma heavy chain V and CH1 region, partial [Mus musculus]", retrieved from the internet on Jun. 30, 2015 at http://ncbi.nlm.nih.gov, 2 pages.
PDB Accession. No. 4LU5_L, "Chain L, Structure of Marine Igg2a A20g2-fab in Compiex With Vaccinia Antigen A33r At Resolution of 2.9 Angstroms", retrieved from the internet on Jun. 30, 2016 at http://www.ncbi.nlm.nih.gov, 3 pages.
Supplementary European Search Report and Opinion, EP 14768059.9, dated Oct. 21, 2016.
Canadian Office Action corresponding to CA 2906551, dated Nov. 27, 2019 (4 pp).

\* cited by examiner

```
HUMAN :   1   MAFVCLAIGCLYTFLISTTFGCTSSSDTEIKVNPPQDFEIVDPGYLGYLYLQWQPPLSLD
              MAF+ L +G LYT L+ T FG +    S+ EIKVNPPQDFEIVDPGYLGYL LQWQPPL  D
DOG   :   1   MAFIHLDVGFLYTLLVCTAFG-SMLSNAEIKVNPPQDFEIVDPGYLGYLSLQWQPPLFPD

HUMAN :  61   HFKECTVEYELKYRNIGSETWKTI ITKNLHYKDGFDLNKGIEAKI HTLLPWQCTNGSEVQ
              +FKECT+EYELKYRNI  SE WKTI ITKNLHYKDGFDLNKGIEAKI+TLLP QCTNGSEV+   PEPTIDE 1
DOG   :  60   NFKECTIEYELKYRNIDSENWKTI ITKNLHYKDGFDLNKGIEAKINTLLPAQCTNGSEVR

HUMAN : 121   SSWAETTYWISPQGIPETKVQDMDCVYYNWQYLLCSWKPGIGVLLDTNYNLFYWYEGLDH
              SSWAETTYW SPQG  ETK+QDMDCVYYNWQYL+CSWKPG+GV  DTNY LFYWYEGLDH
DOG   : 120   SSWAETTYWTSPQGNRETKIQDMDCVYYNWQYLVCSWKPGMGVHFDTNYQLFYWYEGLDH

HUMAN : 181   ALQCVDYIKADGQNIGCRFPYLEA SDYKDFYICVNGSSENKPIRSSYFTFQLNIVKPLP
              + +C DYIK +G+N+GCRFPYLE+ SDYKDFYICVNGSSE +PIR SYF FQLNIVKP+P    PEPTIDE 3
DOG   : 180   SAECTDYIKVNGKNMGCRFPYLES SDYKDFYICVNGSSE SQPIRPSYFIFQLNIVKPMP

HUMAN : 241   PVYLTFTRESSCEIKLKWSIPLGPIPARCFDYEIEIREDDTTLVTATVENETYTLKTTNE
              P YL+ T ++S EI LKW++P GPIPA+CF YEIE  ED TT VT TVENE   +T+NE
DOG   : 240   PDYLSLTVKNSEEINLKWNMPKGPIPAKCFIYEIEFTEDGTTWVTTVENEIQITRTSNE

HUMAN : 301   TRQLCFVVRSKVNIYC DDGIWSEWSDKQC WEGEDLSKKTLLRFWLPFGFILILVIFVTG
              +++LCF+VRSKVNIYC DDGIWSEWSD+QC W+G D+ K+TL+ F  +PF F+ I V+ +T    PEPTIDE 2
DOG   : 300   SQKLCFLVRSKVNIYC DDGIWSEWSDEQC WKG-DIWKETLVFFLIPFAFVSIFVLVITC

HUMAN : 361   LLLRKPNTYPKMI 373
              LLL K    K I
DOG   : 359   LLLYKQRALLKTI 371
```

Fig. 2A

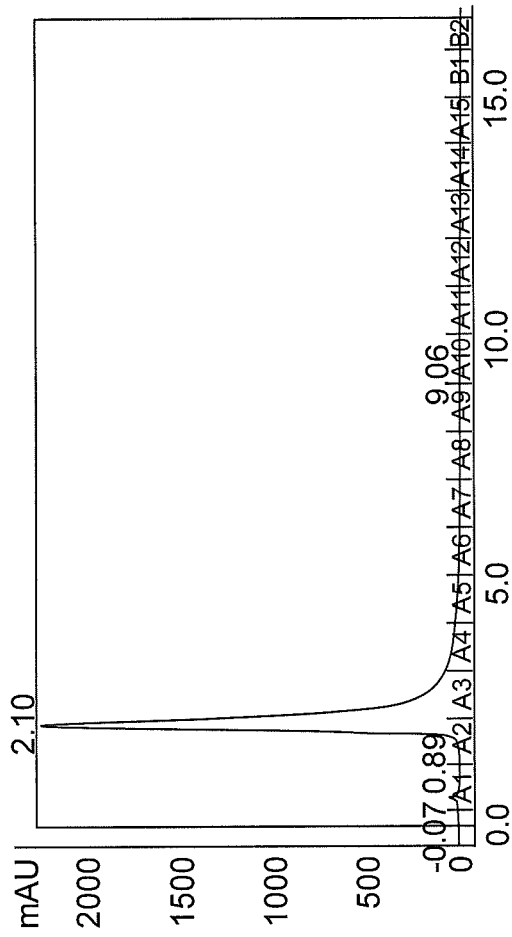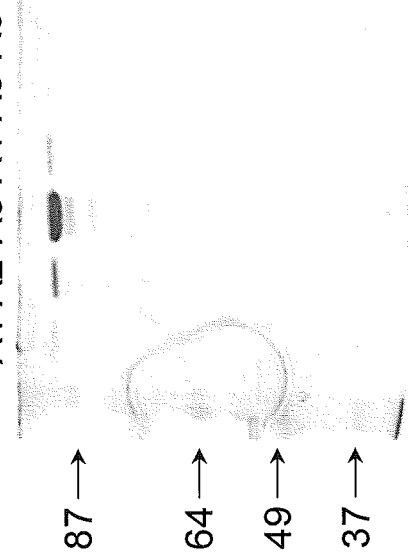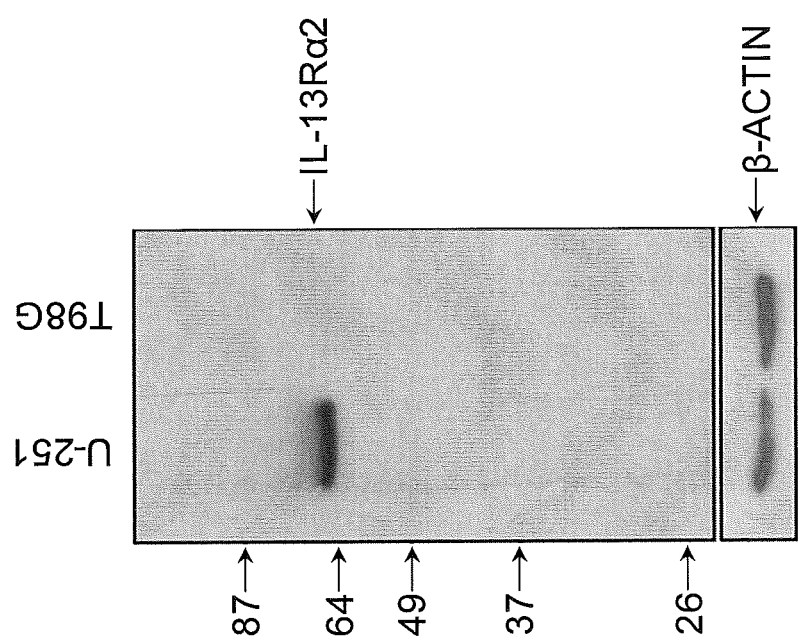
Fig. 3B
Fig. 3C
Fig. 3A

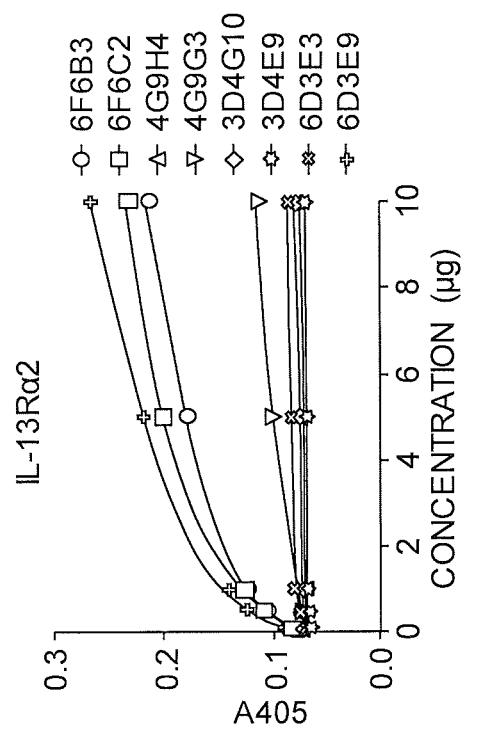
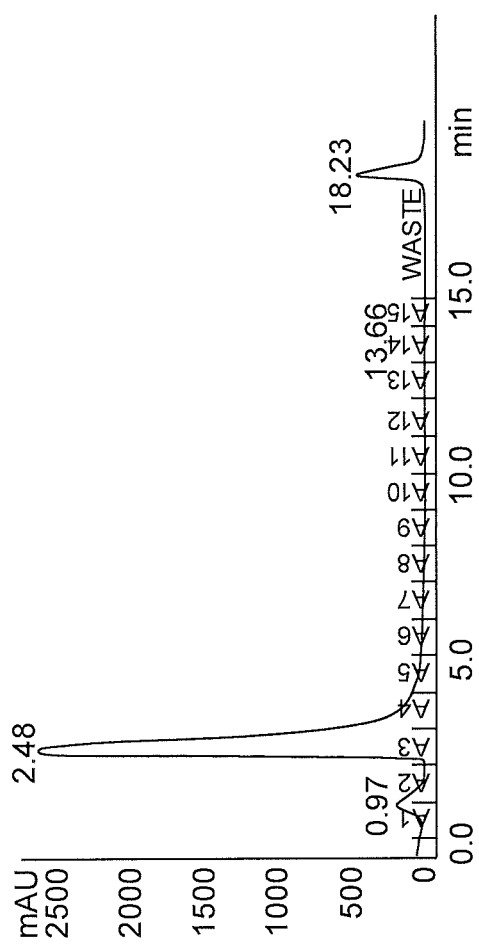
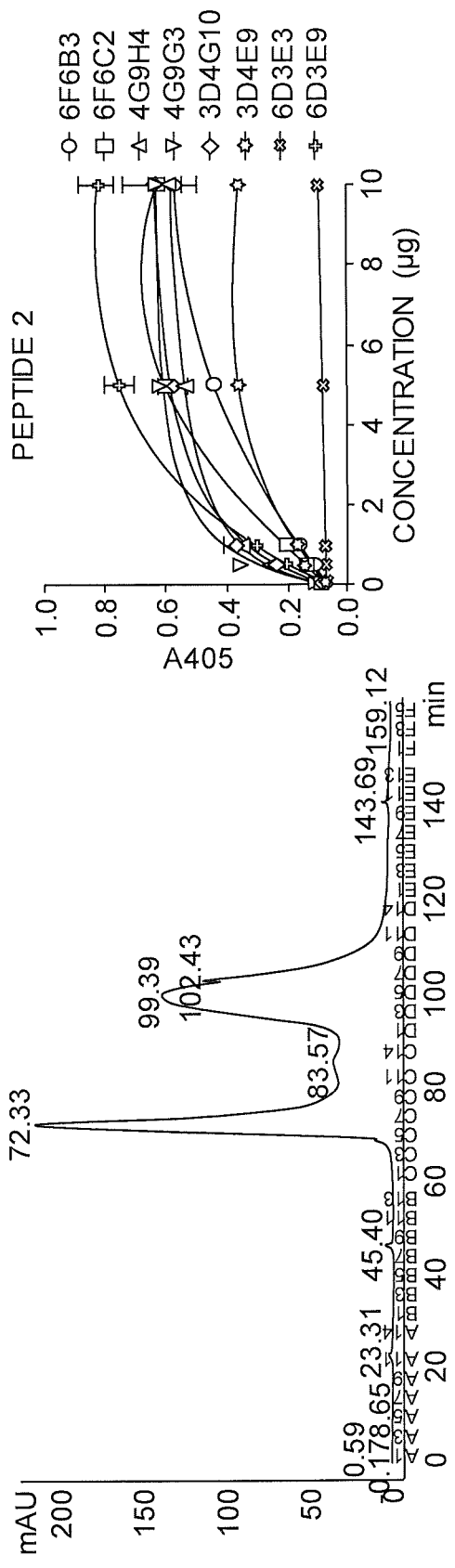

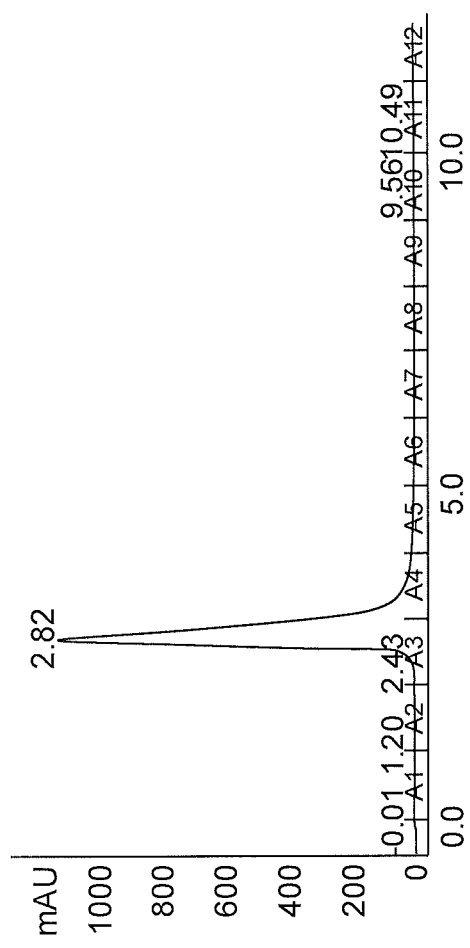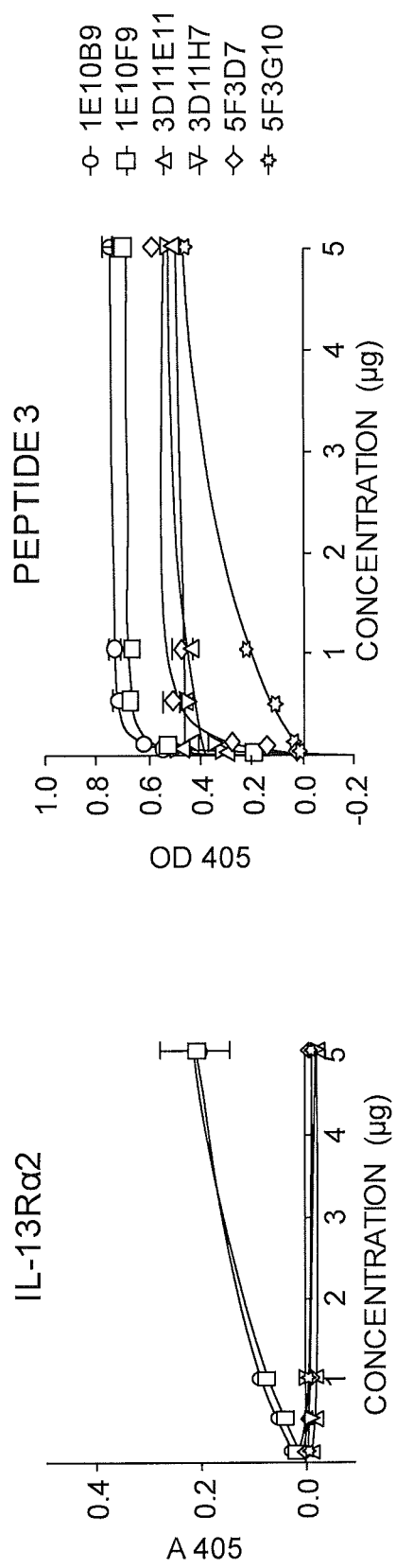
Fig. 7A
Fig. 7B
Fig. 7C

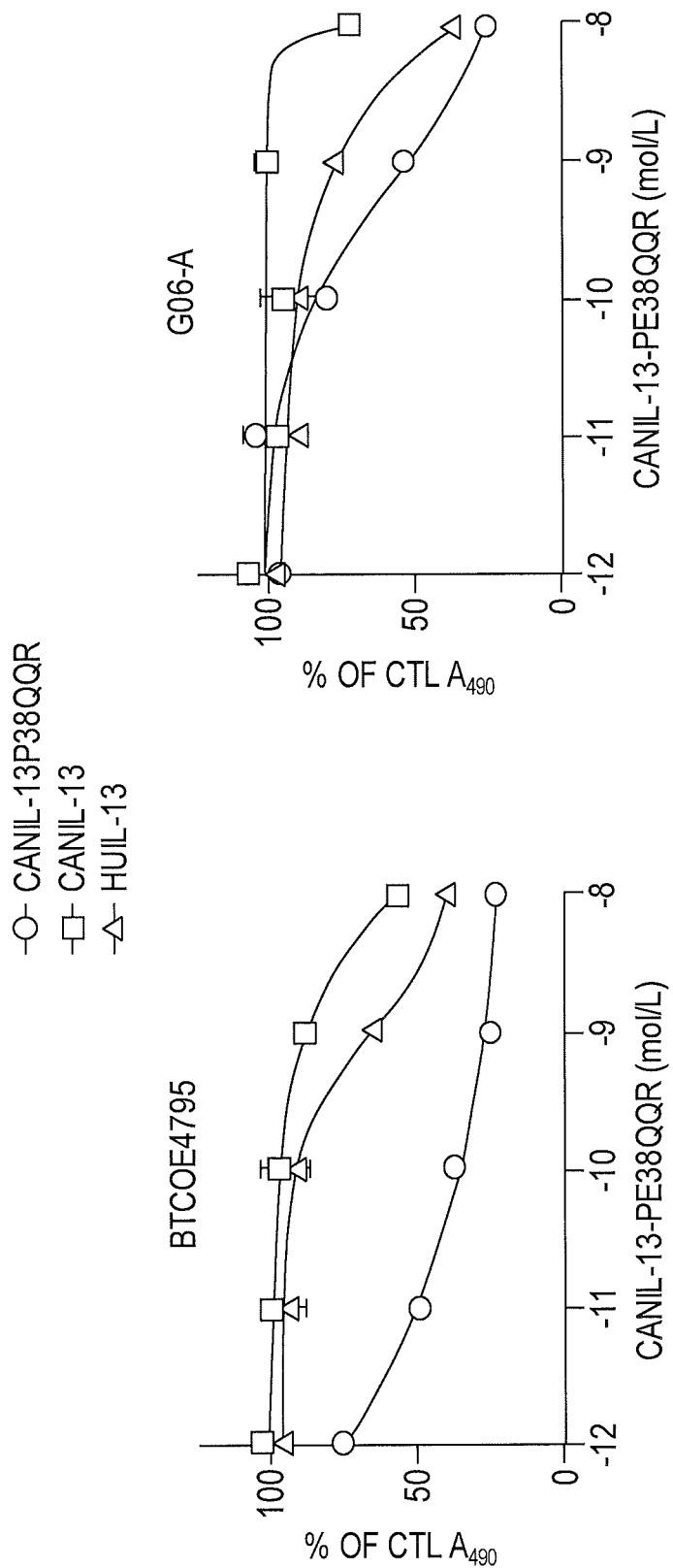

SEQUENCE LISTING

<160> NUMBER OF SEQ ID NOS: 12

<210> SEQ ID NO 1
<211> LENGTH: 21
<212> TYPE: PRT

```
<213> ORGANISM: Artificial
<220> FEATURE:
<223> OTHER INFORMATION: Immunogenic peptide sequence

<400> SEQUENCE: 1

Thr Lys Asn Leu His Tyr Lys Asp Gly Phe Asp Leu Asn Lys Gly Ile
1               5                   10                  15

Glu Ala Lys Ile Cys
            20

<210> SEQ ID NO 2
<211> LENGTH: 14
<212> TYPE: PRT
<213> ORGANISM: Artificial
<220> FEATURE:
<223> OTHER INFORMATION: Immunogenic peptide sequence

<400> SEQUENCE: 2

Ser Asp Asp Gly Ile Trp Ser Glu Trp Ser Asp Lys Gln Cys
1               5                   10

<210> SEQ ID NO 3
<211> LENGTH: 15
<212> TYPE: PRT
<213> ORGANISM: Artificial
<220> FEATURE:
<223> OTHER INFORMATION: Immunogenic peptide sequence

<400> SEQUENCE: 3

Ser Asp Tyr Lys Asp Phe Tyr Ile Cys Val Asn Gly Ser Ser Glu
1               5                   10                  15

<210> SEQ ID NO 4
<211> LENGTH: 26
<212> TYPE: DNA
<213> ORGANISM: Artificial
<220> FEATURE:
<223> OTHER INFORMATION: RT-PCR primer sequence

<400> SEQUENCE: 4
ttcattcatt tggatgtcgg attcct                                          26

<210> SEQ ID NO 5
<211> LENGTH: 24
<212> TYPE: DNA
<213> ORGANISM: Artificial
<220> FEATURE:
<223> OTHER INFORMATION: RT-PCR primer sequence

<400> SEQUENCE: 5
cagggtccac tatctcaaaa tcct                                            24

<210> SEQ ID NO 6
<211> LENGTH: 16
<212> TYPE: DNA
<213> ORGANISM: Artificial
<220> FEATURE:
<223> OTHER INFORMATION: RT-PCR probe sequence

<400> SEQUENCE: 6
atgctgtgca aacaag                                                     16

<210> SEQ ID NO 7
<211> LENGTH: 327
<212> TYPE: DNA
<213> ORGANISM: Artificial
```

```
<220> FEATURE:
<223> OTHER INFORMATION: MAb 1E10B9 variable light chain DNA sequence

<400> SEQUENCE: 7
ccactcattt tgtcagttac cattggacaa ccagcctcta tctcttgcaa gtcaagtcag      60
agcgtcttat atagtaatgg aaaaacctat ttgaattggt tattacagag gccaggccag     120
tctccaaagc gcctaatcta tctggtgtct aaactggact ctggagtccc tgacaggttc     180
actggcagtg gatcaggaac agattttaca ttgaaaatca gcagtggagg gctgaagat     240 ttgggagttt attactgcgt gcaaggttca catttccgt acacgttcgg aggggggacc     300
aagctggaaa taaaacgggc tgatgct                                         327

<210> SEQ ID NO 8
<211> LENGTH: 116
<212> TYPE: PRT
<213> ORGANISM: Artificial
<220> FEATURE:
<223> OTHER INFORMATION: MAb 1E10B9 variable light chain protein
      sequence

<400> SEQUENCE: 8

Glu Ile Val Met Thr Gln Thr Pro Leu Ile Leu Ser Val Thr Ile Gly
1               5                   10                  15

Gln Pro Ala Ser Ile Ser Cys Lys Ser Ser Gln Ser Val Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Ser His Phe Pro Tyr Thr Phe Gly Gly Gly Thr Lys Leu Glu Ile Lys
            100                 105                 110

Arg Ala Asp Ala
        115

<210> SEQ ID NO 9
<211> LENGTH: 324
<212> TYPE: DNA
<213> ORGANISM: Artificial
<220> FEATURE:
<223> OTHER INFORMATION: MAb 1E10B9 variable heavy chain DNA sequence

<400> SEQUENCE: 9
ggacctgagc tgaagaagcc tggagagaca gtcaagatct actgcaaggc ttctggttat      60
tccttcagag actattcagt gcactgggtg aaacaggctc aggaaaggg tttaaagtgg     120 atgggctgga taaatactga gactggtgaa ccaacatatg tggatgaatt caagggacga     180
tttgccttct ttttggaagc ctctgccaac actgtctatt gcagatcag caacctcaaa     240 aatgaggaca cggctacata tttctgtgac taccgtttta cttactgggg ccaggggact     300
ctggtcactg tctctgcagc caaa                                            324

<210> SEQ ID NO 10
<211> LENGTH: 108
<212> TYPE: PRT
<213> ORGANISM: Artificial
```

```
<220> FEATURE:
<223> OTHER INFORMATION: MAb 1E10B9 variable heavy chain protein
      sequence

<400> SEQUENCE: 10

Gly Pro Glu Leu Lys Lys Pro Gly Glu Thr Val Lys Ile Tyr Cys Lys
1               5                   10                  15

Ala Ser Gly Tyr Ser Phe Arg Asp Tyr Ser Val His Trp Val Lys Gln
                20                  25                  30

Ala Pro Gly Lys Gly Leu Lys Trp Met Gly Trp Ile Asn Thr Glu Thr
            35                  40                  45

Gly Glu Pro Thr Tyr Val Asp Glu Phe Lys Gly Arg Phe Ala Phe Phe
        50                  55                  60

Leu Glu Ala Ser Ala Asn Thr Val Tyr Leu Gln Ile Ser Asn Leu Lys
65                  70                  75                  80

Asn Glu Asp Thr Ala Thr Tyr Phe Cys Asp Tyr Arg Phe Thr Tyr Trp
                85                  90                  95

Gly Gln Gly Thr Leu Val Thr Val Ser Ala Ala Lys
                100                 105

<210> SEQ ID NO 11
<211> LENGTH: 373
<212> TYPE: PRT
<213> ORGANISM: Homo sapiens

<400> SEQUENCE: 11

Met Ala Phe Val Cys Leu Ala Ile Gly Cys Leu Tyr Thr Phe Leu Ile
1               5                   10                  15

Ser Thr Thr Phe Gly Cys Thr Ser Ser Asp Thr Glu Ile Lys Val
                20                  25                  30

Asn Pro Pro Gln Asp Phe Glu Ile Val Asp Pro Gly Tyr Leu Gly Tyr
            35                  40                  45

Leu Tyr Leu Gln Trp Gln Pro Pro Leu Ser Leu Asp His Phe Lys Glu
        50                  55                  60

Cys Thr Val Glu Tyr Glu Leu Lys Tyr Arg Asn Ile Gly Ser Glu Thr
65                  70                  75                  80

Trp Lys Thr Ile Ile Thr Lys Asn Leu His Tyr Lys Asp Gly Phe Asp
                85                  90                  95

Leu Asn Lys Gly Ile Glu Ala Lys Ile His Thr Leu Leu Pro Trp Gln
            100                 105                 110

Cys Thr Asn Gly Ser Glu Val Gln Ser Ser Trp Ala Glu Thr Thr Tyr
        115                 120                 125

Trp Ile Ser Pro Gln Gly Ile Pro Glu Thr Lys Val Gln Asp Met Asp
    130                 135                 140

Cys Val Tyr Tyr Asn Trp Gln Tyr Leu Leu Cys Ser Trp Lys Pro Gly
145                 150                 155                 160

Ile Gly Val Leu Leu Asp Thr Asn Tyr Asn Leu Phe Tyr Trp Tyr Glu
                165                 170                 175

Gly Leu Asp His Ala Leu Gln Cys Val Asp Tyr Ile Lys Ala Asp Gly
            180                 185                 190

Gln Asn Ile Gly Cys Arg Phe Pro Tyr Leu Glu Ala Ser Asp Tyr Lys
        195                 200                 205

Asp Phe Tyr Ile Cys Val Asn Gly Ser Ser Glu Asn Lys Pro Ile Arg
    210                 215                 220

Ser Ser Tyr Phe Thr Phe Gln Leu Gln Asn Ile Val Lys Pro Leu Pro
225                 230                 235                 240
```

```
Pro Val Tyr Leu Thr Phe Thr Arg Glu Ser Ser Cys Glu Ile Lys Leu
                245                 250                 255
Lys Trp Ser Ile Pro Leu Gly Pro Ile Pro Ala Arg Cys Phe Asp Tyr
            260                 265                 270
Glu Ile Glu Ile Arg Glu Asp Asp Thr Thr Leu Val Thr Ala Thr Val
        275                 280                 285
Glu Asn Glu Thr Tyr Thr Leu Lys Thr Asn Glu Thr Arg Gln Leu
    290                 295                 300
Cys Phe Val Val Arg Ser Lys Val Asn Ile Tyr Cys Ser Asp Asp Gly
305                 310                 315                 320
Ile Trp Ser Glu Trp Ser Asp Lys Gln Cys Trp Glu Gly Glu Asp Leu
                325                 330                 335
Ser Lys Lys Thr Leu Leu Arg Phe Trp Leu Pro Phe Gly Phe Ile Leu
            340                 345                 350
Ile Leu Val Ile Phe Val Thr Gly Leu Leu Leu Arg Lys Pro Asn Thr
        355                 360                 365
Tyr Pro Lys Met Ile
    370

<210> SEQ ID NO 12
<211> LENGTH: 371
<212> TYPE: PRT
<213> ORGANISM: Canis familiaris

<400> SEQUENCE: 12

Met Ala Phe Ile His Leu Asp Val Gly Phe Leu Tyr Thr Leu Val
1               5                   10                  15
Cys Thr Ala Phe Gly Ser Met Leu Ser Asn Ala Glu Ile Lys Val Asn
                20                  25                  30
Pro Pro Gln Asp Phe Glu Ile Val Asp Pro Gly Tyr Leu Gly Tyr Leu
            35                  40                  45
Ser Leu Gln Trp Gln Pro Pro Leu Phe Pro Asp Asn Phe Lys Glu Cys
    50                  55                  60
Thr Ile Glu Tyr Glu Leu Lys Tyr Arg Asn Ile Asp Ser Glu Asn Trp
65                  70                  75                  80
Lys Thr Ile Ile Thr Lys Asn Leu His Tyr Lys Asp Gly Phe Asp Leu
                85                  90                  95
Asn Lys Gly Ile Glu Ala Lys Ile Asn Thr Leu Leu Pro Ala Gln Cys
            100                 105                 110
Thr Asn Gly Ser Glu Val Arg Ser Ser Trp Ala Glu Thr Thr Tyr Trp
        115                 120                 125
Thr Ser Pro Gln Gly Asn Arg Glu Thr Lys Ile Gln Asp Met Asp Cys
    130                 135                 140
Val Tyr Tyr Asn Trp Gln Tyr Leu Val Cys Ser Trp Lys Pro Gly Met
145                 150                 155                 160
Gly Val His Phe Asp Thr Asn Tyr Gln Leu Phe Tyr Trp Tyr Glu Gly
                165                 170                 175
Leu Asp His Ser Ala Glu Cys Thr Asp Tyr Ile Lys Val Asn Gly Lys
            180                 185                 190
Asn Met Gly Cys Arg Phe Pro Tyr Leu Glu Ser Ser Asp Tyr Lys Asp
        195                 200                 205
Phe Tyr Ile Cys Val Asn Gly Ser Ser Glu Ser Gln Pro Ile Arg Pro
    210                 215                 220
Ser Tyr Phe Ile Phe Gln Leu Gln Asn Ile Val Lys Pro Met Pro Pro
```

-continued

```
                225                 230                 235                 240

Asp Tyr Leu Ser Leu Thr Val Lys Asn Ser Glu Glu Ile Asn Leu Lys
                245                 250                 255

Trp Asn Met Pro Lys Gly Pro Ile Pro Ala Lys Cys Phe Ile Tyr Glu
                260                 265                 270

Ile Glu Phe Thr Glu Asp Gly Thr Thr Trp Val Thr Thr Thr Val Glu
                275                 280                 285

Asn Glu Ile Gln Ile Thr Arg Thr Ser Asn Glu Ser Gln Lys Leu Cys
                290                 295                 300

Phe Leu Val Arg Ser Lys Val Asn Ile Tyr Cys Ser Asp Asp Gly Ile
305                 310                 315                 320

Trp Ser Glu Trp Ser Asp Glu Gln Cys Trp Lys Gly Asp Ile Trp Lys
                325                 330                 335

Glu Thr Leu Val Phe Phe Leu Ile Pro Phe Ala Phe Val Ser Ile Phe
                340                 345                 350

Val Leu Val Ile Thr Cys Leu Leu Leu Tyr Lys Gln Arg Ala Leu Leu
                355                 360                 365

Lys Thr Ile
        370
```

ANTIBODIES AGAINST HUMAN AND CANINE IL-13RA2

RELATED APPLICATIONS

This application is a divisional of U.S. patent application Ser. No. 14/776,356, filed Sep. 14, 2015, now U.S. Pat. No. 9,868,788, which is a 35 U.S.C. § 371 national phase entry of PCT Application PCT/US2014/027254, filed Mar. 14, 2014, and published in English on Sep. 24, 2014, as International Publication No. WO 2014/152361, which claims the benefit of U.S. Provisional Application No. 61/788,312, filed Mar. 15, 2013, the disclosure of each of which is incorporated herein by reference in its entirety.

STATEMENT OF GOVERNMENT SUPPORT

The present invention was made with government support under Grant Number RO1 CA 741451 from the National Institutes of Health. The U.S. Government has certain rights to this invention.

STATEMENT REGARDING ELECTRONIC FILING OF A SEQUENCE LISTING

A Sequence Listing in ASCII text format, submitted under 37 C.F.R. § 1.821, entitled 9151-191TSv2_ST25.txt, 11,485 bytes in size, generated on Jun. 29, 2016, and filed via EFS-Web, is provided in lieu of a paper copy. This Sequence Listing is hereby incorporated by reference into the specification for its disclosures.

BACKGROUND

Glioblastoma (GBM) is a high-grade astrocytoma and represents the most common form of primary brain tumor in humans. The successful treatment of patients with GBM is still a major challenge with a median survival rate of 14.5 months after diagnosis (Stupp et al., Radiotherapy plus concomitant and adjuvant temozolomide for glioblastoma, N Engl J Med 352: 987-996, 2005).

Interleukin 13 receptor alpha 2 (IL-13RA2) is richly over-expressed in GBM (Debinski et al., Human glioma cells overexpress receptor for interleukin 13 and are extremely sensitive to a novel chimeric protein composed of interleukin 13 and *Pseudomonas* exotoxin. Clin Cancer Res 1: 1253-1258, 1995; Debinski et al., Receptor for interleukin 13 is a marker and therapeutic target for human high grade gliomas. Clin Cancer Res 5: 985-990, 1999; Mintz et al., IL13Rα2 is a glioma-restricted receptor for IL13. Neoplasia 4: 388-399, 2002). This receptor is different from the physiological receptor for IL-13 (IL-4A/IL-13RA1 heterodimer), because it is a monomer and binds only IL-13, and not IL-4, its homologue (Debinski, An immune regulatory cytokine receptor and glioblastoma multiforme: an unexpected link. Crit Rev Oncog 9: 255-268, 1998). IL-13RA2 belongs to a group of cancer/testis like tumor antigens (Debinski and Gibo, Molecular expression analysis of restrictive receptor for interleukin 13, a brain tumor-associated cancer/testis antigen. Mol Med 6: 440-449, 2000) and is one of the downstream gene targets following activation of both wild type EGFR and mutant EGFRvIII (Hu et al., Cytokine up-regulation of IL-13Rα2 in GBM cells leads to an increased potency of recombinant IL13 cytotoxin. Cancer Therapy 3: 531-542, 2005; Lal et al., Mutant epidermal growth factor receptor up-regulates molecular effectors of tumor invasion. Cancer Res 62: 3335-3339, 2002). Demethylation causes up-regulation of IL-13RA2 suggesting epigenetic mechanisms are also involved in IL-13RA2 receptor regulation (Mintz and Debinski, Cancer genetics/epigenetics and the X chromosome: Possible new links for malignant glioma pathogenesis and immune-based therapies. Critic Rev Oncogen 11: 77-95, 2000) in addition to activation of PI3K and ERK pathways (Hu et al., Cytokine up-regulation of IL-13Rα2 in GBM cells leads to an increased potency of recombinant IL13 cytotoxin. Cancer Therapy 3: 531-542, 2005).

Several molecular therapies targeting IL-13Rα2 have been generated and all have the potential of being applied to management of patients with GBM. Among them are vaccines (Okano et al., Identification of a novel HLA-A*0201-restricted, cytotoxic T lymphocyte epitope in a human glioma-associated antigen, interleukin 13 receptor α2 chain. Clin Cancer Res 8: 2851-2855, 2002; Mintz et al., Protein and DNA-based active immunotherapy targeting interleukin 13 receptor alpha 2. Cancer Biother and Radiopharm 23: 581-589, 2008), re-targeted cytotoxic T cells (Kahlon et al., Specific recognition and killing of glioblastoma multiforme by interleukin 13-zetakine redirected cytolytic T cells. Cancer Res 64:9160-9167, 2004) and new rationally designed IL-13 based cytotoxins (Chunbin et al., Targeting glioblastoma multiforme with an IL-13/diphtheria toxin fusion protein in vitro and in vivo in nude mice. Prot Engin 15: 419-427, 2002; Debinski et al., Novel anti-brain tumor cytotoxins specific for cancer cells. Nature Biotech 16: 449-453, 1998; Mintz et al., Molecular targeting with recombinant cytotoxins of interleukin-13 receptor alpha-2-expressing glioma. J Neuro-Oncol 64: 117-123, 2003). Additionally, novel IL-13RA2-targeted adenoviral and herpes virus constructs have been developed and could potentially be used as gene therapy vectors for the treatment of gliomas (Zhou et al., Genetic engineering of a herpes virus 1 vector dependent on the IL-13Rα2 receptor for entry into cells: interaction of glycoprotein D with its receptors is independent of the fusion of the envelope and the plasma membrane. Proc Natl Acad Sci 99: 15124-15129, 2002; Ulasov et al., Novel recombinant adenoviral vector that targets the interleukin-13 receptor alpha2 chain permits effective gene transfer to malignant glioma. Hum Gene Ther 18: 118-129, 2007; Candolfi et al., Gene therapy-mediated delivery of targeted cytotoxins for glioma therapeutics. Proc Natl Acad Sci 107: 20021-20026, 2010). Thus, IL-13RA2 is a truly attractive molecular target, being over-expressed in a majority of, but not all, patients with GBM (Wykosky et al., IL-13 Receptor alpha-2, EphA2, and Fra-1 as molecular denominators of high-grade astrocytomas and specific targets for combinatorial therapy. Clin. Cancer Res 14: 199-208, 2008).

IL-13RA2 is also overexpressed in a variety of peripheral tumors, such as pancreatic cancer, gastric cancer, head and neck cancer, etc., and has been implicated in tumor metastasis.

BRIEF SUMMARY OF EMBODIMENTS

Provided herein is an antibody (e.g., an isolated antibody) that specifically binds an epitope (e.g., linear epitope) within amino acids spanning the extracellular portion of human IL-13RA2. In some embodiments, the amino acids spanning the extracellular portion of human IL-13RA2 have at least 90% identity with the corresponding canine sequence of IL-13RA2. In some embodiments, the antibody specifically binds both human and canine IL-13RA2.

In some embodiments, the epitope is within amino acids of SEQ ID NO: 1 (Peptide 1). In some embodiments, the epitope is within amino acids of SEQ ID NO: 2 (Peptide 2). In some embodiments, the epitope is within amino acids of SEQ ID NO: 3 (Peptide 3). In some embodiments, the epitope may comprise at least 4, 5, 6, 7, 8, 9, 10, 11, 12, 13 or 14 consecutive amino acids from SEQ ID NO:1, SEQ ID NO:2, or SEQ ID NO:3.

In some embodiments, the antibody is a monoclonal antibody. In some embodiments, the antibody is a recombinant antibody. In some embodiments, the antibody is humanized.

In some embodiments, the antibody is the monoclonal antibody produced by hybridoma 1E10B9 or a recombinant form thereof.

In some embodiments, the antibody comprises a variable light chain amino acid sequence of SEQ ID NO:8, or at least 90% identity thereto; and/or a variable heavy chain amino acid sequence of SEQ ID NO:10, or at least 90% identity thereto.

In some embodiments, the antibody is coupled to a detectable group. In some embodiments, the antibody is coupled to a chemotherapeutic agent (e.g., a bacterial toxin or derivative thereof, such as PE38QQR).

Also provided is a composition comprising an antibody as taught herein and a pharmaceutically acceptable carrier. In some embodiments, the carrier is an aqueous carrier (e.g., saline).

Further provided is a method of treating a tumor in a subject in need thereof (e.g., a human or canine subject) comprising administering an antibody as taught herein to said subject in a treatment effective amount. In some embodiments, the tumor comprises cells having elevated IL-13RA2 expression as compared to the corresponding non-cancerous cells.

In some embodiments, the tumor is a brain tumor. In some embodiments, the brain tumor is an astrocytoma (e.g., glioblastoma multiforme (GBM)), meningioma or oligodendroglioma. In some embodiments, the antibody is administered to said subject by intra-cerebral administration. In some embodiments, the antibody is administered by intracerebroventricular infusion. In some embodiments, the antibody is administered by intrathecal infusion. In some embodiments, the antibody is administered into the brain of said subject by convection-enhanced delivery (CED).

In some embodiments, the tumor is breast cancer, ovarian cancer, kidney cancer, bladder cancer, pancreatic cancer, gastric cancer, colorectal cancer, head and neck cancer, thyroid cancer, prostate cancer, or Kaposi's sarcoma.

Still further provided is a method of inhibiting cancer metastasis in a subject in need thereof (e.g., a human or canine subject) comprising administering an antibody as taught herein to said subject in a treatment effective amount. In some embodiments, the cancer comprises cells having elevated IL-13RA2 expression as compared to the corresponding non-cancerous cells.

In some embodiments, the tumor is a brain tumor. In some embodiments, the brain tumor is an astrocytoma (e.g., glioblastoma multiforme (GBM)), meningioma or oligodendroglioma. In some embodiments, the antibody is administered to said subject by intra-cerebral administration. In some embodiments, the antibody is administered by intracerebroventricular infusion. In some embodiments, the antibody is administered by intrathecal infusion. In some embodiments, the antibody is administered into the brain of said subject by convection-enhanced delivery (CED).

In some embodiments, the tumor is breast cancer, ovarian cancer, kidney cancer, bladder cancer, pancreatic cancer, gastric cancer, colorectal cancer, head and neck cancer, thyroid cancer, prostate cancer, or Kaposi's sarcoma.

Further provided method of detecting a cancer in a subject in need thereof comprising administering an antibody as taught herein coupled to a detectable group to said subject in an amount effective to detect said antibody.

BRIEF DESCRIPTION OF THE DRAWINGS

FIG. 2A. Alignment of human (SEQ ID NO:11) and canine (SEQ ID NO:12) sequences of IL-13RA2. A, The sequences were obtained from the NCBI database. The regions of the two species that were utilized as immunogens are boxed.

FIG. 3A, Western blot of U-251 MG and T98G human GBM cell lysates using media of 3G12C3 hybridoma cells. FIG. 3B, Example of Protein A chromatography used for purification of MAb 2G12C3. FIG. 3C, The fractions of purified antibody 3G12C3 corresponding to the peak in B as determined by 10% SDS-PAGE.

FIG. 6A to FIG. 6F. Purification and immunoreactivity of MAbs obtained with immunization using Peptide 2. Protein G and S-200 Size exclusion column purification of MAbs 6F6B3 IgG1, FIG. 6A; and 6D3E9 IgM, FIG. 6B; respectively. Reactivity of MAbs raised against Peptide 2 in ELISA using recombinant IL-13Rα2-Fc, FIG. 6C; and Peptide 2, FIG. 6D. Detection of recombinant IL-13Rα2, but not of IL-13Rα1-Fc with MAbs 6D3E9, 4G9G3 and 3D4G10, FIG. 6E Immunofluorescence in G48a cells using MAb 6D3E9, FIG. 6F.

FIG. 7A to FIG. 7I. Purification and immunoreactivity of MAbs obtained with immunization using Peptide 3. Protein G purification of MAb 1E10B9, FIG. 7A. Reactivity of MAbs raised against Peptide 3 in ELISA using recombinant IL-13RA2-Fc, FIG. 7B; and the synthetic Peptide 3, FIG. 7C. Detection of IL-13RA2, but not of IL-13RA1-Fc with MAbs 1E10B9 and 1E10F9, FIG. 7D Immunoreactive IL-13RA2 in Western blot of U-251 MG and T98G cell lysates using MAb 1E10B9, FIG. 7E. Expression of IL-13RA2 detected by immunohistochemistry using MAb 1E10B9 in a human GBM specimen (BTCOE 4631) or G48a xenograft growing in nude mice FIG. 7F, canine GBM, FIG. 7G, canine astrocytoma, FIG. 7H, and oligodendrogliomas, FIG. 7I.

FIG. 9A to FIG. 9G. Production and testing of canIL-13 and canIL-13 based cytotoxin. Superimposition of canIL-13 and huIL-13 molecules, (3D reconstruction using JMol), FIG. 9A. Purified canIL-13 and canIL-13 cytotoxin, (10% SDS-PAGE), FIG. 9B. Activation of TF-1 cells proliferation by cytokines, FIG. 9C. Cytotoxicity of canIL-13 cytotoxin and its neutralization on G48a human GBM cells, FIG. 9D. Cytotoxicity of canIL-13 cytotoxin on human and canine GBM cells, FIG. 9E. Cytotoxicity of canIL-13 cytotoxin on human GBM established (U-251 MG) and low passage human GBM cells (BTCOE 4706) and canine GBM cells (G06-A), FIG. 9F and FIG. 9G. CTL—control. Vertical bars represent SEM and if not seen, they are smaller than the points.

DETAILED DESCRIPTION OF EMBODIMENTS

Figure 1:
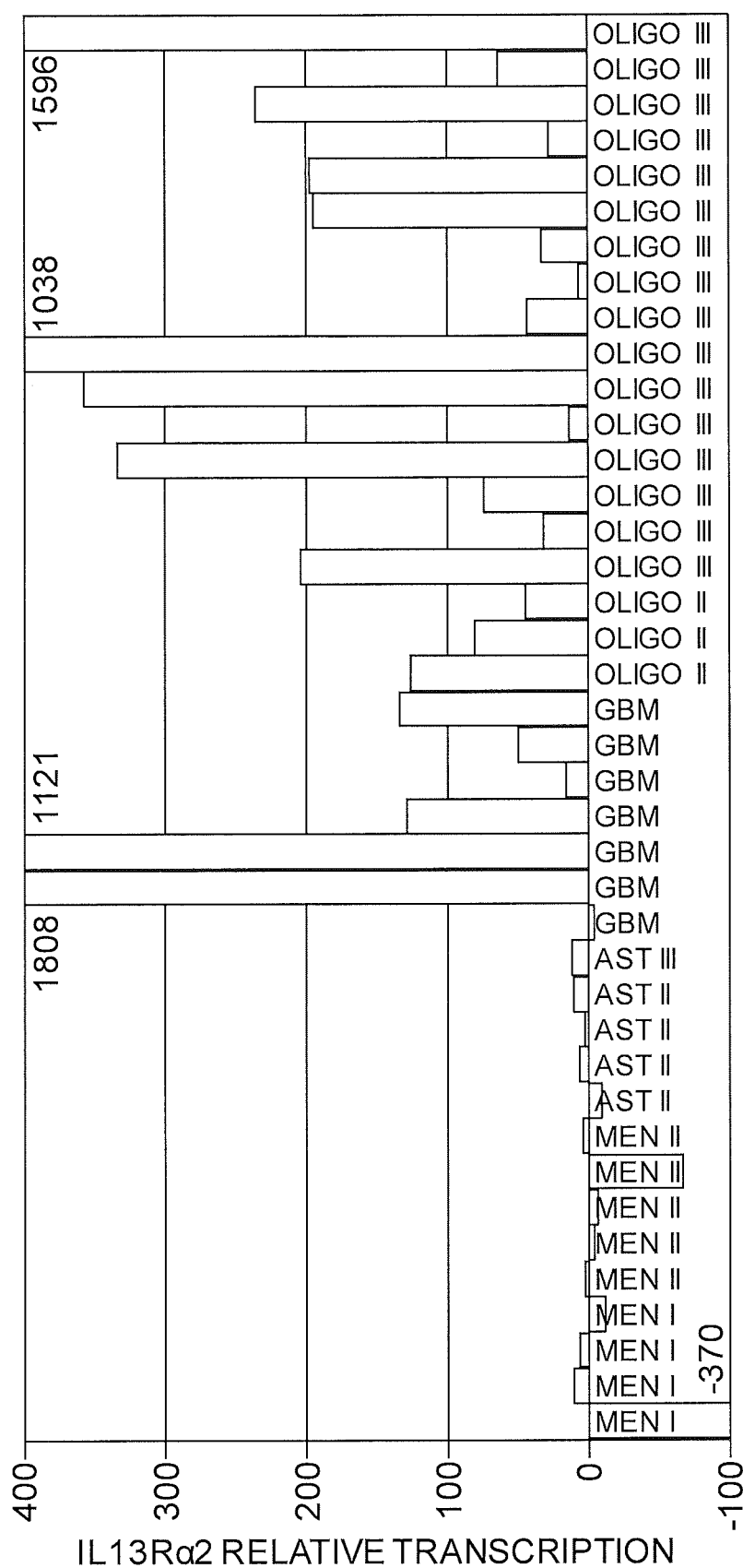
FIG. 1. Quantitative TaqMan RT-PCR comparing expression of IL-13RA2 in canine primary brain tumors. Elevated expression, relative to normal brain cortex, is seen predominantly in high grade glial tumors, essentially mirroring protein expression determined by western blotting. MEN—meningioma; AST—astrocytoma; GBM—glioblastoma multiforme; OLIGO—oligodendroglioma.

The present invention is directed to antibodies that specifically bind to both human and canine IL-13RA2, as well as compositions comprising the same and methods of using the same in the treatment of cancers of the central nervous system as well as peripheral cancers. In some embodiments, the cancer is positive for or over-expresses IL-13RA2.

In some embodiments, the cancer is a "brain tumor." The cancer can be a primary or secondary brain cancer. Cancer treatable with embodiments of the present invention include, but not limited to, astrocytoma, oligodendroglioma, ependymoma, meningiomas, acoustic neuroma/schwannomas, and medulloblastoma. Also included is neuroblastoma. In some embodiments, the cancer is a secondary brain cancer which has metastasized from a non-brain cancer.

Other cancers known to overexpress IL-13RA2 for which the antibodies may be used include, but are not limited to, peripheral solid tumors such as breast cancer, ovarian cancer, kidney cancer, bladder cancer, pancreatic cancer, gastric cancer, colorectal cancer, head and neck cancer, thyroid cancer, prostate cancer, and Kaposi's sarcoma.

The antibodies also find use in fusion proteins, e.g., coupled to a toxin for cancer cell-specific delivery thereof. The antibodies may also be coupled to a detectable group to facilitate imaging of the cancerous tissues.

All references cited are incorporated by reference to the extent they are consistent with the disclosure provided herein.

As used herein, "a," "an" or "the" can mean one or more than one. For example, "a" cell can mean a single cell or a multiplicity of cells.

Also as used herein, "and/or" refers to and encompasses any and all possible combinations of one or more of the associated listed items, as well as the lack of combinations when interpreted in the alternative ("or").

Furthermore, the term "about," as used herein when referring to a measurable value such as an amount of a compound or agent of this invention, dose, time, temperature, and the like, is meant to encompass variations of ±20%, ±10%, ±5%, ±1%, ±0.5%, or even ±0.1% of the specified amount.

"Brain cancer" or "brain tumor" may be any stage, grade, histomorphological feature, invasiveness, aggressivity or malignancy of an affected tissue or cell aggregation in any part of the central nervous system (i.e., brain and spinal cord). In some embodiments, the brain tumor is a glioma. In some embodiments, the tumor is an anaplastic astrocytoma, anaplastic oligoastrocytoma or anaplastic oligodendroglioma, in particular, fibrillary astrocytoma WHO grade II, oligoastrocytoma WHO grade II, oligodendroglioma grade II, anaplastic astrocytoma WHO grade III, anaplastic oligoastrocytoma WHO grade III, anaplastic oligodendroglioma grade III or glioblastoma, such as glioblastoma multiforme (see, e.g., US Patent Application Publication No. 2010/0291590).

Gliomas are tumors occurring in the glial cells, which help support and protect critical areas of the brain. Gliomas are the most common type of brain tumor in adults, responsible for about 42% of all adult brain tumors. Gliomas are further characterized by the types of cells they affect, into the categories of astrocytoma (affecting astrocytes), oligodendroglioma (affecting oligodendrocytes), ependymoma (affecting ependymal cells), meningiomas (affecting the meninges), acoustic neuroma/schwannoma (affecting Schwann's cells), and medulloblastoma (affective cells in the cerebellum). See also U.S. 2013/0012452 to Basile et al.

Astrocytomas are graded from I to IV depending on the speed of progression. Grade I (pilocytic astrocytoma) is slow growing, with little tendency to infiltrate surrounding brain tissue. Grade II (diffuse astrocytoma) is fairly slow-growing, with some tendency to infiltrate surrounding brain tissue. Grade III (anaplastic/malignant astrocytoma) tumors grow rather quickly and infiltrate surrounding brain tissue. Grade IV (glioblastoma multiforme, GBM) is an extremely aggressive and lethal form of brain cancer. Unfortunately, it is the most common form of brain tumor in adults, accounting for about 67% of all astrocytomas.

Oligodendrogliomas, which make up 4% of brain tumors, mostly affect people over 45 years of age. Some subtypes of this tumor are particularly sensitive to treatment with radiation therapy and chemotherapy. Half of patients with oligodendrogliomas are still alive after five years.

Ependymomas are rare; about 2% of all brain tumors, but are the most common brain tumor in children. They generally do not affect healthy brain tissue and do not spread beyond the ependyma. Although these tumors respond well to surgery, particularly those on the spine, ependymomas cannot always be completely removed. The five-year survival rate for patients over age 45 approaches 70%.

Meningiomas affect the meninges, the tissue that forms the protective outer covering of the brain and spine. One-quarter of all brain and spinal tumors are meningiomas, and up to 85% of them are benign.

Malignant gliomas are a fatal disease with an average life-expectancy following diagnosis of less than one year.

The prognosis for patients with high-grade gliomas is very poor, and is especially so for older patients. Of Americans diagnosed each year with malignant gliomas, about half are alive 1 year after diagnosis, and 25% after two years. Those with anaplastic astrocytoma survive about three years. Glioblastoma multiforme has the worst prognosis, with a life expectancy of less than 9-15 months following diagnosis.

"Subjects" are inclusive of human subjects, as well as animal subjects, particularly mammalian subjects such as dogs, for veterinary purposes. While subjects may be of any suitable age, the subjects are in some embodiments neonatal, infant, juvenile, adolescent, adult, or geriatric subjects. In some embodiments, human subjects are at least 50, 60, 65, or 70 years of age.

"Treat" as used herein refers to any type of treatment that imparts a benefit to a subject, particularly delaying or retarding the progression of the disease or cancer. For example, the treatment may kill or otherwise decrease the number of cells and/or volume of cancerous tissue in the brain or central nervous system, inhibit or slow the progression of the cancer, alleviate side effects such as cognitive abnormalities, etc. In some embodiments, treating specifically includes prophylactic treatment to prevent, delay or otherwise inhibit tumor metastasis.

"Pharmaceutically acceptable" as used herein means that the compound or composition is suitable for administration to a subject to achieve the treatments described herein, without unduly deleterious side effects in light of the severity of the disease and necessity of the treatment.

1. Active Agents.

Provided herein as active agents are antibodies that specifically bind to both the human and canine IL-13RA2, inclusive of such antibodies coupled to another agent (e.g., a chemotherapeutic agent and/or detectable group). In some embodiments, the antibody specifically binds an epitope within amino acids spanning the extracellular portion of human IL-13RA2 (inclusive of the amino acids at each end). In some embodiments, the antibody specifically binds an epitope within or comprising the amino acids of SEQ ID NO: 1 (Peptide 1), SEQ ID NO: 2 (Peptide 2), or SEQ ID NO: 3 (Peptide 3), or a portion thereof. For example, the epitope may comprise at least 4, 5, 6, 7, 8, 9, 10, 11, 12, 13 or 14 consecutive amino acids from SEQ ID NO:1, SEQ ID NO:2, or SEQ ID NO:3.

"IL13" or "IL-13" as used herein refers to interleukin-13, which is a pleiotropic cytokine. IL-13 has approximately 30% sequence identity with IL4 and exhibits IL4-like activities on monocytes/macrophages and human B cells (Minty et al. (1993) Nature 362:248; McKenzie et al. (1987) Proc. Natl. Acad. Sci. USA 90:3735). In particular, IL-13 appears to be a potent regulator of inflammatory and immune responses. IL-13 can up-regulate the monocyte/macrophage expression of CD23 and MHC class I and class II antigens, down-regulate the expression of Fcγ, and inhibit antibody-dependent cytotoxicity. IL-13 can also inhibit nitric oxide production as well as the expression of pro-inflammatory cytokines (e.g., IL-1, IL-6, IL-8, IL-10 and IL-12) and chemokines (MIP-1, MCP), but enhance the production of IL-1.

"Interleukin 13 receptor A2" or (IL-13RA2 or IL-13Rα2) is a receptor for IL-13 that is richly over-expressed in a variety of tumors. Researchers have found that IL-13RA2 is directly involved in cancer invasion and metastasis in cancers such as human pancreatic cancer, colorectal cancer and ovarian cancer. See, e.g., Nakashima et al., J. Immunol. 187 (2011); Barderas et al., Cancer Res. 72(11):2780-90 (2012); Fujisawa et al., Int. J. Cancer 131(2):344-56 (2012).

The term "antibody" as used herein refers to immunoglobulin molecules and immunologically active portions of immunoglobulin molecules, i.e., molecules that contain an antigen binding site that specifically binds an antigen, whether natural or partly or wholly synthetically produced. The term also covers any polypeptide or protein having a binding domain which is, or is homologous to, an antibody binding domain. These can be derived from natural sources, or they may be partly or wholly synthetically produced. Examples of antibodies are fragments which comprise an antigen binding domain, such as Fab, scFv, Fv, dAb, Fd; and diabodies.

In some embodiments, antibodies of the present invention are internalized by the target cancer cells.

In some embodiments, the antibody is a monoclonal antibody. In some embodiments, the monoclonal antibody can be a monoclonal antibody produced by a hybridoma as taught herein, e.g., hybridoma 1E10B9. In some embodiments, the monoclonal antibody can be a monoclonal antibody or fragment thereof that competes for binding to the same epitope specifically bound by the monoclonal antibody produced by a hybridoma taught herein, e.g., the hybridoma 1E10B9.

In some embodiments, the monoclonal antibody or a fragment thereof is a chimeric antibody or a humanized antibody. In additional embodiments, the chimeric or humanized antibody comprises at least a portion of the complementarity determining regions (CDRs) of the monoclonal antibody produced by a hybridoma as taught herein, such as hybridoma 1E10B9. As used herein, a "portion" of a CDR is defined as one or more of the three loops from each of the light and heavy chain that make up the CDRs (e.g., from 1-6 of the CDRs) or one or more portions of a loop comprising, consisting essentially of, or consisting of at least three contiguous amino acids. For example, the chimeric or humanized antibody may comprise 1, 2, 3, 4, 5, or 6 CDR loops, portions of 1, 2, 3, 4, 5, or 6 CDR loops, or a mixture thereof. Methods for making humanized antibodies are described in, for example, U.S. Pat. No. 5,225,539.

In some embodiments, the antibody is recombinant. A "recombinant" protein is a protein such an antibody produced by a recombinant nucleic acid. "Recombinant" nucleic acid as used herein refers to a nucleic acid produced by combining two or more nucleic acid sequences from different sources, e.g., by use of molecular biology techniques, to form a new nucleic acid, e.g., a "heterologous" nucleic acid. The recombinant nucleic acid may be provided in the form of a "vector" or "delivery vector" in order to transform or transfect cells to contain the new nucleic acid. As used herein, a "vector" or "delivery vector" can be a viral or non-viral vector that is used to deliver a nucleic acid to a cell, tissue or subject.

In some embodiments, the antibody includes a variable light chain DNA sequence of SEQ ID NO:7, or a DNA sequence that has at least 80, 85, 90, 95, 97, 98, or 99% identity with SEQ ID NO:7. In some embodiments, the antibody includes a variable heavy chain DNA sequence of SEQ ID NO:9, or a DNA sequence that has at least 80, 85, 90, 95, 97, 98, or 99% identity with SEQ ID NO:9.

In some embodiments, the antibody includes a variable light chain amino acid sequence of SEQ ID NO:8, or an amino acid sequence that has at least 80, 85, 90, 95, 97, 98, or 99% identity with SEQ ID NO:8. In some embodiments, the antibody includes a variable heavy chain amino acid sequence of SEQ ID NO:10, or an amino acid sequence that has at least 80, 85, 90, 95, 97, 98, or 99% identity with SEQ ID NO:10.

An "isolated" protein or polypeptide means a protein or polypeptide that is separated or substantially free from at least some of the other components of the naturally occurring organism or virus, for example, the cell or viral structural components or other proteins or nucleic acids commonly found associated with the protein. As used herein, the "isolated" protein or polypeptide is at least 25%, 30%, 40%, 50%, 60%, 70%, 75%, 80%, 85%, 90%, 95%, 97%, 98%, 99% or more pure (w/w).

"Chemotherapeutic agent" as used herein includes, but is not limited to, any agent useful in the treatment of cancer. Examples include, but are not limited to, a cytotoxic agent, methotrexate, daunomycin, mitomycin C, cisplatin, vincristine, epirubicin, fluorouracil, verapamil, cyclophosphamide, cytosine arabinoside, aminopterin, bleomycin, mitomycin C, democolcine, etoposide, mithramycin, chlorambucil, melphalan, daunorubicin, doxorubicin, tamosifen, paclitaxel, vincristin, vinblastine, camptothecin, actinomycin D, and cytarabine. Further examples are found in U.S. Patent Application Publication 2006/0121539 (Debinski et al.), which is incorporated by reference herein in its entirety.

"Cytotoxic agent" or "toxic agent" as used herein includes, but is not limited to, maytansinoids and maytansinoid analogs, taxoids, CC-1065 and CC-1065 analogs, dolastatin and dolastatin analogs, ricin (or more particularly the ricin A chain), aclacinomycin, diphtheria toxin, Monensin, Verrucarin A, Abrin, Tricothecenes, and *Pseudomonas* exotoxin A, taxol, cytochalasin B, gramicidin D, ethidium bromide, emetine, mitomycin, etoposide, tenoposide, antimitotic agents, such as the vinca alkaloids (e.g., vincristine and vinblastine), colchicin, anthracyclines, such as doxorubicin and daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof, antimetabolites (e.g., methotrexate, 6-mercaptopurine, 6-thioguanine, cytarabine, and 5-fluorouracil decarbazine), alkylating agents (e.g., mechlorethamine, thioepa chlorambucil, melphalan, carmustine (BSNU), lomustine (CCNU), cyclothosphamide, busulfan, dibromomannitol, streptozotocin, mitomycin C, and cis-dichlorodiamine platinum (II) (DDP)), and antibiotics, including, but not limited to, dactinomycin (formerly actinomycin), bleomycin, mithramycin, calicheamicin, and anthramycin (AMC)).

In some embodiments, cytotoxic agents include "bacterial toxins" such as *Pseudomonas* exotoxin, ricin, abrin, ribonuclease (RNase), DNase I, Staphylococcal enterotoxin-A, pokeweed antiviral protein, gelonin, diphtheria toxin, etc. See, e.g., U.S. Pat. No. 7,517,964. In some embodiments, *Pseudomonas* exotoxin or a diphtheria toxin are preferred. See U.S. Pat. No. 5,328,984 to Pastan et al. and U.S. Pat. No. 6,296,843 to Debinski, which are each incorporated by reference herein in its entirety. *Pseudomonas* exotoxins can include, but are not limited to, *Pseudomonas* exotoxin A (PE). The *Pseudomonas* exotoxin can be modified such that it substantially lacks domain Ia, and in some embodiments *Pseudomonas* exotoxins include PE38QQR and PE4E. Diphtheria toxins can include DT390, a diphtheria toxin in which the native binding domain is eliminated. It will be appreciated that in various embodiments, the therapeutic agents can be attached to, e.g., the amino terminus or the carboxyl terminus.

2. Pharmaceutical Formulations.

The active agents described herein may be formulated for administration in a pharmaceutical carrier in accordance with known techniques. See, e.g., Remington, *The Science And Practice of Pharmacy* ($9^{th}$ Ed. 1995). In the manufacture of a pharmaceutical formulation according to the invention, the active agent (including pharmaceutically acceptable salts thereof) is typically admixed with, inter alia, an acceptable carrier. The carrier must, of course, be acceptable in the sense of being compatible with any other ingredients in the formulation and must not be deleterious to the patient. The carrier may be a solid or a liquid, or both, and is preferably formulated with the compound as a unit-dose formulation, for example, a tablet, which may contain from 0.01 or 0.5% to 95% or 99% by weight of the active agent. One or more active agents may be incorporated in the formulations of the invention, which may be prepared by any of the well known techniques of pharmacy comprising admixing the components, optionally including one or more accessory ingredients.

The formulations of the invention include those suitable for oral, rectal, topical, buccal (e.g., sub-lingual), vaginal, parenteral (e.g., subcutaneous, intramuscular, intradermal, or intravenous), topical (i.e., both skin and mucosal surfaces, including airway surfaces) and transdermal administration, although the most suitable route in any given case will depend on the nature and severity of the condition being treated and on the nature of the particular active agent which is being used.

Formulations of the present invention suitable for parenteral administration comprise sterile aqueous and non-aqueous injection solutions of the active compound, which preparations are preferably isotonic with the blood of the intended recipient. These preparations may contain antioxidants, buffers, bacteriostats and solutes that render the formulation isotonic with the blood of the intended recipient. Aqueous and non-aqueous sterile suspensions may include suspending agents and thickening agents. The formulations may be presented in unit\dose or multi-dose containers, for example sealed ampoules and vials, and may be stored in a freeze-dried (lyophilized) condition requiring only the addition of the sterile liquid carrier, for example, saline or water-for-injection immediately prior to use. Extemporaneous injection solutions and suspensions may be prepared from sterile powders, granules and tablets of the kind previously described. For example, in one aspect of the present invention, there is provided an injectable, stable, sterile composition comprising an active compound or composition in a unit dosage form in a sealed container. The compound or composition is provided in the form of a lyophilizate that is capable of being reconstituted with a suitable pharmaceutically acceptable carrier to form a liquid composition suitable for injection thereof into a subject. The unit dosage form typically comprises from about 10 mg to about 10 grams of the compound or composition. When the compound or composition is substantially water-insoluble, a sufficient amount of emulsifying agent that is physiologically acceptable may be employed in sufficient quantity to emulsify the compound or composition in an aqueous carrier. One such useful emulsifying agent is phosphatidyl choline.

Further, the present invention provides liposomal formulations. The technology for forming liposomal suspensions is well known in the art. When the active agent is provided in an aqueous-soluble form, using conventional liposome technology, the same may be incorporated into lipid vesicles. In such an instance, due to the water solubility, the active agent will be substantially entrained within the hydrophilic center or core of the liposomes. The lipid layer employed may be of any conventional composition and may either contain cholesterol or may be cholesterol-free. When the active agent is water-insoluble, again employing conventional liposome formation technology, the salt may be substantially entrained within the hydrophobic lipid bilayer which forms the structure of the liposome. In either instance, the liposomes which are produced may be reduced in size, as through the use of standard sonication and homogenization techniques.

The liposomal formulations containing the active agents disclosed herein, may be lyophilized to produce a lyophilizate, which may be reconstituted with a pharmaceutically acceptable carrier, such as water, to regenerate a liposomal suspension.

Other pharmaceutical compositions may be prepared, such as aqueous base emulsions. In such an instance, the composition will contain a sufficient amount of pharmaceutically acceptable emulsifying agent to emulsify the desired amount of the active agent. Particularly useful emulsifying agents include phosphatidyl cholines, and lecithin.

Further provided are active agents in the form of an implant which provides continuous administration as the implant dissolves and/or the agent is eluted from the implant. The implant may be placed during surgery in accordance with known methods. See, e.g., Perry et al., "Glidel wafers in the treatment of malignant glioma: a systemic review," Curr. Oncol. 14(5): 189-194 (2007).

In addition to active agent(s), the pharmaceutical compositions may contain other additives, such as pH-adjusting additives. In particular, useful pH-adjusting agents include acids, such as hydrochloric acid, bases and/or buffers, such as sodium lactate, sodium acetate, sodium phosphate, sodium citrate, sodium borate, or sodium gluconate. Further, the compositions may contain microbial preservatives. Useful microbial preservatives include methylparaben, propylparaben, and benzyl alcohol. The microbial preservative is typically employed when the formulation is placed in a vial designed for multidose use. As indicated, the pharmaceutical compositions of the present invention may be lyophilized using techniques well known in the art.

3. Dosage and Routes of Administration.

As noted above, the present invention provides pharmaceutical formulations comprising active agents (including the pharmaceutically acceptable salts thereof), which may be provided in pharmaceutically acceptable carriers for administration. The carrier in some embodiments is a liquid carrier suitable for infusion. The carrier may be, for example, an aqueous carrier (e.g., comprising water, such as a saline solution).

Particular routes of parenteral administration include intrathecal injection, including directly into the tumor or a tumor resection cavity, and intraventricular injection into a ventricle of the brain.

Active compounds and compositions may be administered by intratumor injection (including tumors in any region such as tumors of the brain), or in the case of brain tumors injection into a ventricle of the brain.

In some embodiments, the active agent is administered directly into the brain (i.e., within the blood brain barrier) and/or other portions of the central nervous system of a subject. In some embodiments, the active agent is administered to the subject intra-cerebrally. In some embodiments, the active agent is administered to the subject by intracerebroventricular infusion. In some embodiments, the active agent is administered by intrathecal delivery. In some embodiments, the active agent is administered by convection-enhanced delivery.

Convection-enhanced delivery (CED) is the continuous injection under positive pressure of a fluid containing a therapeutic agent. In the central nervous system (CNS), this delivery technique circumvents the blood-brain barrier in delivering agents. See, e.g., US 2012/0041394 to Haider et al.; US 2012/0209110 to Bankiewicz et al. CED uses a fluid pressure gradient established at the tip of an infusion catheter and bulk flow to propagate substances within the extracellular fluid space. CED allows the extracellularly-infused material to further propagate via the perivascular spaces and the rhythmic contractions of blood vessels acting as an efficient motive force for the infusate. As a result, a higher concentration of drug can be distributed more evenly over a larger area of targeted tissue than would be seen with a simple injection. CED has been clinically tested in the fields of neurodegenerative diseases and neurooncology, and covers a broad field of applications, such as the delivery of small molecules, macromolecules, viral particles, magnetic nanoparticles, and liposomes.

In some embodiments, the active agent is administered in combination with radiation therapy. In some embodiments, the active agent is administered in combination with surgery to remove all or part of the cancerous tissue. In some embodiments, the active agent is administered in combination with another chemotherapy agent. See U.S. Pat. No. 5,677,178. Chemotherapeutic agents may be administered by methods well known to the skilled practitioner, including systemically, direct injection into the cancer, or by localization at the site of the cancer by associating the desired chemotherapeutic agent with an appropriate slow release material or intra-arterial perfusing of the tumor. The preferred dose may be chosen by the practitioner based on the nature of the cancer to be treated, and other factors routinely considered in administering. See, e.g., U.S. Pat. No. 7,078,030.

Subjects may also be treated by radiation therapy, including, but not limited to, external beam radiotherapy, which may be at any suitable dose (e.g., 20 to 70 Gy or more per tumor, typically delivered over a fractionated schedule).

As used herein, the administration of two or more therapies (inclusive of active agents, other chemotherapeutics, radiation therapy, etc., or any combination thereof) "in combination" means that the two are administered closely enough in time that the administration of or presence of one alters the biological effects of the other. The therapies may be administered simultaneously (concurrently) or sequentially.

Simultaneous administration of the agents may be carried out by mixing the agents prior to administration, or by administering the agents at the same point in time but at different anatomic sites or using different routes of administration, or administered at times sufficiently close that the results observed are indistinguishable from those achieved when the agents are administered at the same point in time. Simultaneous administration of one or more agents with radiation may be carried out by administering the compounds at the same point in time as the radiation is applied, or at times sufficiently close that the results observed are indistinguishable from those achieved when the compounds and radiation are administered at the same point in time.

Sequential administration of the agents may be carried out by administering the agents at different points in time, e.g., an active agent at some point in time prior to or after administration of one or more other chemotherapeutics, such that the administration of agent enhances the therapeutic effect of cancer treatment. In some embodiments, an active agent is administered at some point in time prior to the initial administration of another chemotherapeutic or other therapy. Alternatively, the other therapeutic or therapy may be administered at some point in time prior to the administration of an active agent, and optionally, administered again at some point in time after the administration of an active agent.

In some embodiments, the antibody as taught herein is coupled to a chemotherapeutic agent. In some embodiments, the agent is a *Pseudomonas* exotoxin or diphtheria toxin or a derivative thereof. See U.S. Pat. No. 8,362,207 to Debinski et al., which is incorporated by reference herein in its entirety.

In some embodiments, the antibody as taught herein is coupled to a detectable group or label. "Label" or "detectable group" as used herein may be any suitable label or detectable group detectable by spectroscopic, photochemical, biochemical, immunochemical, electrical, optical or chemical means including but not limited to biotin, fluorophores, antigens, porphyrins, and radioactive isotopes. Labels useful in the present invention include biotin for staining with labeled avidin or streptavidin conjugate, magnetic beads (e.g., Dynabeads™), fluorescent dyes (e.g., fluorescein, fluorescein-isothiocyanate [FITC], Texas red, rhodamine, green fluorescent protein, enhanced green fluorescent protein, lissamine, phycoerythrin, Cy2, Cy3, Cy3.5, Cy5, Cy5.5, Cy7, FluorX [Amersham], SyBR Green I & II [Molecular Probes], and the like), radiolabels (e.g., $^3$H, $^{35}$S, $^{14}$C, or $^{32}$P), enzymes (e.g., hydrolases, particularly phosphatases such as alkaline phosphatase, esterases and glycosidases, or oxidoreductases, particularly peroxidases such as horseradish peroxidase, and the like), substrates, cofactors, inhibitors, chemiluminescent groups, chromogenic agents, and calorimetric labels such as colloidal gold or colored glass or plastic (e.g., polystyrene, polypropylene, latex, etc.) beads.

In some embodiments, the active agent is administered to the subject in an amount of from about 50, 100, or 200 to about 300 or 400 mg/kg. In some embodiments, the active agent is administered to the subject in an amount of from about 0.1, 0.5, 1 or 5, to about 10, 25, 50 or 100 mg/kg. In some embodiments, such as for an immunotoxin that can work at nanomolar concentrations, the active agent is administered to the subject in an amount of from about 0.01, 0.05, 0.1 or 0.5, to about 1, 5, 10 or 20 mg/kg. In some embodiments, the active agent may be administered 1 to 5, 6, or 7 times weekly, e.g., for a period of from about 4 to about 6 weeks per cycle, up to about 4 to about 6 cycles. In some embodiments, the active agent is administered as a continuous or substantially continuous infusion for at least 2 or at least 3 days. In some embodiments, the active agent is administered as a continuous or substantially continuous infusion in a range of from about 5, 6, 7 or 8, to about 10, 12, 14 or 16 days. For example, the active agent may be administered as a continuous infusion for about 7-14 days, which may be repeated as desired (e.g., repeated every 4-6 weeks).

As a general proposition, the initial pharmaceutically effective amount of the active agent administered parenterally will be in the range of about 0.1 to 50 mg/kg of patient body weight per day, with the typical initial range of antibody used being 0.3 to 20 mg/kg/day, more preferably 0.3 to 15 mg/kg/day. The desired dosage can be delivered by a single bolus administration, by multiple bolus administrations, or by continuous infusion administration of active compound, depending on the pattern of pharmacokinetic decay that the practitioner wishes to achieve.

The active agent(s) is suitably administered to the patient at one time or over a series of treatments. Depending on the type and severity of the disease, about 1 μg/kg to 15 mg/kg (e.g. 0.1-20 mg/kg) of active compound(s) is an initial candidate dosage for administration to the patient, whether, for example, by one or more separate administrations, or by continuous infusion. A typical daily dosage might range from about 0.1, 0.5, 1, 10 or 100 μg/kg up to 100, 200 or 500 mg/kg, or more, depending on the factors mentioned above. For repeated administrations over several days or longer, depending on the condition, the treatment is sustained until a desired suppression of disease symptoms occurs. A more particular dosage of the active compound will be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g., such that the patient receives from about two to about twenty, e.g. about six doses of the antibody). An initial higher loading dose, followed by one or more lower doses may be administered. An exemplary dosing regimen comprises administering an initial loading dose of about 0.5 to 10 mg/kg, followed by a weekly maintenance dose of about 0.5 to 10 mg/kg of the active compound. However, other dosage regimens may be useful. The progress of this therapy is easily monitored by conventional techniques and assays.

The present invention is explained in greater detail in the following non-limiting Examples.

EXAMPLES

Dogs and humans are the only species in which spontaneously arising primary brain tumors are common. Although the true incidence of canine gliomas is not fully known, the frequency of brain tumors in dogs, based on necropsy data, is similar to humans, i.e., approximately 2% (20). Prevalence of nervous system tumors in the general population of pet dogs is also similar and has been estimated at 14.5/100,000 animal years (21-24). Over 70% of primary tumors occur in dogs aged 6 years or more, a period in lifespan comparable to middle age in humans, although they may occur in younger animals as well. Astrocytomas, oligodendrogliomas and invasive meningiomas are most common (25). High-grade astrocytomas, anaplastic oligodendrogliomas, and mixed anaplastic astrocytic oligodendrogliomas, histomorphologically virtually identical to those seen in humans, have been reported. Unfortunately, patterns of survival for dogs with malignant gliomas are similar to those seen in people, with death relatively soon (weeks to months) after diagnosis, for those animals that are not humanely euthanized immediately, at the time of diagnosis (26).

Tumors of the central nervous system in canine patients are spontaneous, heterogenous, progress over clinically relevant periods of time and are large enough to enable clinically relevant translation of both experimental diagnostic and therapeutic clinical procedures developed recently in human patients (27). This is particularly important when considering therapeutic approaches using delivery techniques such as convection enhanced delivery (CED) to large tumor volumes (28-30). With this translational model in mind the goals of the current study were: a) To further validate canine spontaneous brain tumors as a model system for the investigation of IL-13RA2 targeted therapies, b) To generate MAbs against IL-13RA2 that would be cross-reactive between humans and dogs and be more sensitive than commercially available antibodies, and c) To produce a recombinant cytotoxic agent to target the IL-13RA2 in canine tumors in a species-specific manner.

Materials and Methods

Sample Collection:

All canine tumor tissue was obtained from surgical biopsy/resection specimens, necropsy, or from archival paraffin embedded material from clinical cases presented to the Veterinary Medical Teaching Hospitals, University of California, Davis and Virginia-Maryland Regional College of Veterinary Medicine, and the University of Tennessee College of Veterinary Medicine. Samples of tumor from necropsy were collected within 20 minutes of death and snap frozen in liquid nitrogen. Surgical samples were similarly stored following collection. Samples of adjacent tumor tissue were processed for routine paraffin embedding and histology whenever fresh tissue was collected in liquid nitrogen.

Normal brain samples were collected from both necropsy and archival paraffin embedded material. All tumors were graded by a board certified pathologist (RJH) essentially according to the international WHO classification of human tumors of the nervous system (31). Meningiomas were graded as either grade I (benign), grade II (atypical) or grade III (malignant); astrocytomas were graded as either grade II (diffuse), grade III (anaplastic) or grade IV (glioblastoma multiforme); oligodendroglial tumors were graded as either grade II (oligodendroglioma) or grade III (anaplastic oligodendroglioma).

Cell Culture

The canine SDT-3G and GO6A cell lines were derived from spontaneously occurring canine glioblastoma multiforme tumors. The human G48a cell line was derived from a human high grade glioma (32). SDT-3G and GO6A cells were cultured in Dulbecco's Minimal Essential Eagles Medium, high glucose (Invitrogen/Gibco, Carlsbad, Calif.), supplemented to 4825 mg/L sodium bicarbonate (Invitrogen/Gibco, Carlsbad, Calif.), with 10% heat inactivated fetal bovine serum (Invitrogen/Gibco, Carlsbad, Calif.) at 37° C. and 5% CO2. The cells were tested to be free from mycoplasma contamination by PCR.

Quantitative RT-PCR

Total RNA extraction, cDNA preparation and real-time TaqMan PCR were done as previously described (33). IL-13Rα2 PCR primers and probes were designed based on canine sequence data using Primer Express software resulting in a 121 bp product spanning exons 5-6 (Applied Biosystems, Foster City, Calif.) (forward TTCAT-TCATTTGGATGTCGGATTCCT (SEQ ID NO:4); reverse CAGGGTCCACTATCTCAAAATCCT (SEQ ID NO:5); probe ATGCTGTGCAAACAAG (SEQ ID NO:6)). TaqMan PCR primers for canine housekeeping genes glyceraldehydes-3-phosphate dehydrogenase (GAPDH), ribosomal protein L13A, glycosyltransferase (HPRT1), and glucuronidase beta (GUSB) were used as previously described (33). PCR products were designed to be less than 150 base pairs in length, with either one of the primer pairs or internal probe placed over an exon-exon junction to allow discrimination between cDNA and gDNA. Transcript quantitation was done using the comparative CT method and reported as relative transcription, or the n-fold difference relative to the mean value for individual normal cerebral cortex samples (n=15). Tumor samples that had GAPDH CT values weaker than 3 times the average GAPDH CT value were considered low quality cDNA samples and were discarded.

Monoclonal Antibody Production

Amino acid peptides spanning the extracellular portion of human IL-13RA2, with 100% homology between human and canine sequences, were synthesized as immunogen for the study. The peptides were conjugated to keyhole limpet hemocyanin (KLH) and Balb/c mice were immunized and boosted. Titers were measured by ELISA and the most responsive mice were selected for splenocyte fusion. Hybridoma cells were screened by ELISA and the most productive clones were expanded in DMEM with 10% FBS.

Purification of Monoclonal Antibodies

Hybridoma cells were grown in UltraDoma Protein Free media (Lonza). Conditioned media from each monoclonal antibody was collected and loaded by FPLC onto a HiTrap Protein A (for IgG2B) or Protein G (IgG1) HP column (GeHealthcare, Piscataway, N.J.). Antibody was eluted with 100 mM Sodium Citrate pH 4.3 (Protein A) or 100 mM Glycine HCl pH 2.7 (Protein G). IgM isotype antibodies were purified by S-200 size exclusion chromatography. Briefly, conditioned media from the hybridoma cells was buffer exchanged to PBS and concentrated to a final volume of 1 mL. Sample was injected into a calibrated S-200 sepharose column and the IgM antibody was collected in the void volume. The purity of the monoclonal antibodies was verified by SDS-PAGE.

ELISA Assay

ELISA plates were coated overnight at 4° C. with 100 μl/well of 1 mg/ml IL-13RA2-Fc (R&D Systems, Minneapolis, Minn.) or immunogenic peptide (Genscript Corp). Non-bound protein was removed and the plate blocked with blocking buffer (2% milk/PBS) for one hour at room temperature (RT). Blocking buffer was removed and dilutions of antibody made in blocking buffer was added to the wells and allowed to incubate for one hour at room temperature (RT).

Plates were washed with PBS/0.05% Tween and anti-mouse horseradish peroxidase (HRP) secondary antibody was added. After one hour incubation at RT, plates were washed and detection was performed with 2,2'-azino-bis(3-ethylbenzthiazoline-6-sulfonic acid (ABTS). Color was allowed to develop and the plates were read at OD 405 nm.

SDS-PAGE and Western Blot Analyses

Cell lysates were prepared from sub confluent cultures. Cells were washed with PBS and lysed in radioimmunoprecipitation assay buffer (PBS, 0.5% sodium deoxycholate, 0.1% SDS, and 0.5% Igepal) containing mammalian protease inhibitor cocktail (Sigma). Nonmalignant brain and pathologist-verified tumor tissue were minced into small pieces while frozen and homogenized in radioimmunoprecipitation assay buffer with mammalian protease inhibitor cocktail. Lysates were passed through an 18-gauge needle to shear the DNA and were incubated on ice for 60 minutes. Nonsoluble debris was pelleted at 10,000×g for 10 mins and the supernatant was collected and stored at −80° C. until use. Additional normal human brain lysates were purchased from Chemicon International and Clontech Laboratories. Lysates were separated by SDS-PAGE using 10% or 15% acrylamide. Proteins were then transferred to a polyvinylidene difluoride membrane (Perkin Elmer, Waltham, Mass.) and blocked for at least 1 hr with Blotto (5% milk in PBS/0.05% Tween 20). Membranes were incubated with primary antibody diluted in Blotto overnight at 4° C. while shaking. β-actin (1:50,000) antibody was purchased from Sigma. Following three 5-min washes in PBS/0.05% Tween 20, membranes were incubated with secondary antibody conjugated with horseradish peroxidase (goat anti-mouse IgG at a dilution of 1:5,000 in Blotto for 1 hr. Membranes were washed three times for 5 mins each in PBS/0.05% Tween 20 and detection was done using the Enhanced Chemiluminescence Plus Western Blotting Detection System (GeHealthcare, Piscataway, N.J.). Membranes were exposed to autoradiographic film for various times. Films were scanned at 600× dpi and images were compiled using Jasc Paint Shop Pro version 6.0.

Immunoprecipitation

Cell lysates were prepared from sub confluent cultures. Cells were washed with PBS and lysed in radioimmunoprecipitation assay buffer (PBS, 0.5% sodium deoxycholate, 0.1% SDS, and 0.5% Igepal) containing mammalian protease inhibitor cocktail and 1 mmol/L sodium vanadate. Cell lysate (400 μg) was incubated with 10 μg monoclonal antibody overnight at 4° C. Twenty microliters of a 50% PBS/bead slurry containing 10 μL packed protein G-Sepharose beads (Sigma) were added and incubated overnight at 4° C. Beads were collected by centrifugation, washed three times with ice-cold radioimmunoprecipitation assay buffer, and resuspended in 50 μL of 3×SDS sample buffer (New England Biolabs, Ipswich, Mass.). Samples were heated at 100° C. for 5 minutes. Supernatant was collected and stored at −20° C. until separated using SDS-PAGE.

Immunofluorescent Staining

G48a cells, a primary high grade glioma cell line established in this laboratory, were plated and grown overnight on glass slides in RPMI-1640 containing 4 mg glucose/ml and 10% FBS. After 24 hrs, slides were washed in PBS, fixed for 2 min in cold acetone and washed twice in PBS. Slides were washed in PBS for three changes at RT for 5 min each. Cells were blocked for 1 hr in 10% normal goat serum (Invitrogen). Monoclonal antibodies were diluted in PBS/1.5% normal goat serum and incubated overnight at 4° C. Slides were washed in PBS for three changes at RT for 5 min each. Secondary antibody (Anti-mouse Alexa Fluor-488) was applied and incubated at RT for 1 hour. Nuclei were visualized with DAPI. Slides were washed well in PBS and mounted with FluoreGuard MountingMedia (ScyTek).

Xenografts

G48a cells were implanted subcutaneously into the hind flank of female athymic nude (nu/nu) mice at 1×10⁶ cells per mouse in 100 μl of PBS. Tumor measurement was obtained weekly using a digital caliper. When tumors reached a volume exceeding 1000 mm$^3$, mice were euthanized and tumors were removed, fixed in 10% buffered formalin and embedded in paraffin.

Immunohistochemistry

Biopsy specimens of tumors and normal brain tissues were fixed in 10% formalin and embedded in paraffin. Sections were cut at a thickness of 4-6 μm. Slides were heated at 65° C., de-paraffinized in xylene, and re-hydrated. Antigen retrieval was performed with 10 mM sodium citrate buffer, pH 6.0, by microwaving twice for 5 min. Endogenous peroxidase activity and non-specific biotin was quenched with Peroxide Blocking Kit and Biotin Blocking Kit respectively (ScyTek Laboratories, Logan, Utah). Slides were blocked and incubated with primary antibody or matched isotype control overnight at 4° C. Slides were washed with PBS followed by incubation with biotinylated anti-mouse antibody for 15 min, then Avidin-HRP for 20 min (ScyTek). Visualization with NovaRed (Vector Labs) was performed and allowed to develop for 5-10 min. Slides were counterstained with hematoxylin for 1 min, dehydrated and mounted with Permount (Fisher).

Photomicrographs were taken with a 20× or 40× magnification lens on an Olympus IX70 microscope using a Retiga 2000R camera with ImagePro Plus v5.1 software.

Flow Cytometry 1.5×10⁵ cells were blocked with PBS (pH 7.2)/1% BSA for 1 hr at 4° C. Cells were then supplemented with 15 μg of MAb 1E10B9 or mouse IgG1 (Rockland Immunochemicals, Gilbertsville, Pa.) incubated for an additional 2 hrs at 4° C. Cells were then washed in PBS/1% BSA and resuspended in 100 μL PBS/1% BSA containing 4 μg of anti-mouse Alexa Fluor-488 (Invitrogen, Eugene, Oreg.) for 1 hr at 4° C. Samples were washed three times with PBS/BSA before undergoing FLOW analysis on a FACSCalibur (BD Biosciences, San Jose, Calif.).

Recombinant Protein Expression and Purification

Canine IL-13 was cloned from published sequences obtained from Genebank (442990). This cytokine was further cloned in-frame to the N-terminal end of a modified *Pseudomonas* exotoxin A (PE38QQR) to generate a single chain cytotoxin as previously described for human IL-13 (34). *E. coli* BL21 (λDE3) cells were transformed with this plasmid and 1.0 liter of LB broth containing 100 μg ampicillin, 4 g glucose, and 0.4 g MgSO4/1.0 liter culture was grown until log phase. Protein expression was induced with isopropylthio-β-galactoside (IPTG) for 90 min. Inclusion bodies were isolated, denatured in 8M guanidine solution and renatured in a dithioerythritol and oxidized glutathione reduction-oxidation mixture. After dialysis, recombinant proteins were purified by ion exchange chromatography using FPLC (GE Healthcare Biosciences, Piscataway, N.J.).

TF-1 Proliferation Assay

TF-1 cells, a pre-leukemic human B cell line, (ATCC, Manassas, Va.) were grown in the presence of increasing concentrations canIL13 in 96-well culture plates. After 72 hrs of incubation at 37° C., the rate of proliferation of the TF-1 cells was determined by a colorimetric MTS [3-(4,5-dimethylthiazol-2-yl)-5-(3-carboxymethoxyphenyl)-2-(4-sulfophenyl)-2H-tetrazolium, inner salt]/PMS (phenazine methosulfate) cell proliferation assay (Promega, Madison, Wis.).

Cytoxicity and Blocking Assay

Human glioblastoma cell line U-251 MG, human primary glioblastoma cells BTCOE 4795 and canine primary glioblastoma cells (GO6-A and SDT-3G) were plated into 96-well culture plates and allowed to attach overnight. HuIL13 or canIL13 was added to the cells and incubated for 1 h at 37° C. An equal volume of 0.1% bovine serum albumin in PBS was added to cells for assays without blocking ligand. Increasing concentration of the human or canine IL13P38QQR was added and the cells were incubated for 48 hrs. Cell viability was determined using the colorimetric MTS/PMS method. Cells treated with high concentrations of cycloheximide served as background for the assay.

Statistical Analysis of RT-PCR Data

Data were divided into nominal categories of tumor type, and further divided into ordinal categories of grade. Kruskal-Wallis one way analysis of variance was used to compare the variation in expression of IL-13RA2 mRNA among tumor types, and Jonckheere-Terpstra tests were done to compare variation based on grade within tumor types. When significant differences were evident, Mann-Whitney tests were used for pair-wise comparisons. A sequentially rejective modification of Bonferroni's multiple comparison adjustment was used to confirm significant results. Statistical significance was defined as $P<0.05$.

Results

Gene Expression of IL-13RA2 in Primary Canine Brain Tumors.

In expectation that the similarities between human and canine primary brain tumors exist at the genetic/molecular level, we preliminarily screened 40 canine archival tumor specimens for IL13RA2 gene expression (FIG. 1). A total of 15 samples of normal cerebral cortex (4 frozen and 11 paraffin embedded samples) and 40 tumor samples were analyzed (11 frozen and 29 paraffin embedded samples). Of these samples, there were 9 meningiomas (4 Grade I, 5 atypical Grade II); 12 astrocytomas (4 grade II, 1 grade III, 7 GBM) and 19 oligodendrogliomas (3 grade II, 16 Grade III). For all genes analyzed, the averages of normalized values and the standard deviations for both frozen and paraffin embedded samples were not significantly different. Increased expression was seen predominantly in the high grade gliomas (FIG. 1). Differences in expression based on grade were present within the astrocytic tumors, with the highest expression seen in GBMs (p=0.003). Expression in high grade oligodendrogliomas was significantly greater than both meningiomas (grade I and II combined; p<0.0001) and lower grade astrocytomas (grade II and III combined; p=0.0004). Expression in GBMs was also significantly greater than meningiomas (grade I and II combined; p=0.002). There was no significant difference between expression in high grade oligodendrogliomas and GBMs (p=0.97). Thus, we obtained evidence for the over-expression of IL-13RA2 in various canine tumors similarly to humans (35).

MAbs Raised Against Peptide 1 of Homology Region Between Human and Canine IL-13RA2.

To verify the exact expression profile of IL13RA2 in various primary brain tumors, and validate the canine translational model we generated bi-species specific antibodies against IL-13Rα2 against three different regions of the receptor with 100% sequence identity (Table 1).

Figure 4A:
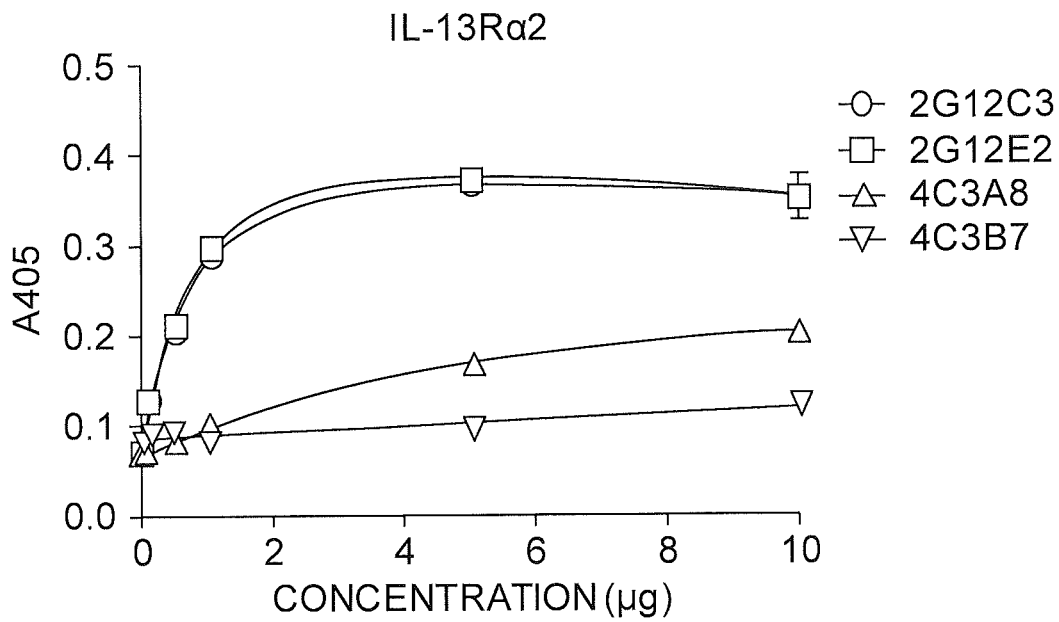
FIG. 4F to FIG. 4H. Recognition of synthetic and recombinant immunogens (FIG. 4A, FIG. 4B) and immunoreactive IL-13RA2 in human and canine brain tumor specimens (FIG. 4C-FIG. 4H) by purified MAb's of Peptide 1. ELISA was conducted using either recombinant IL-13Rα2-Fc, FIG. 4A or the synthetic Peptide 1, FIG. 4B. Human glioblastoma (G), FIG. 4C; oligodendroglioma (O), astrocytoma (A), and normal brain (NB); G14 is a human GBM tumor lysate used as control, FIG. 4D; and meningioma (M), FIG. 4E tissue lysates immunoreactivity using Western blots. Canine astrocytoma, glioblastoma and normal brain, FIG. 4F; oligodendroglioma, gliosarcoma (GSO) and mixed astro-oligo (AO), FIG. 4G; and choroid plexus papilloma (CPP) and meningioma, FIG. 4H tissue lysates immunoreactivity using western blots.
Figure 4B:
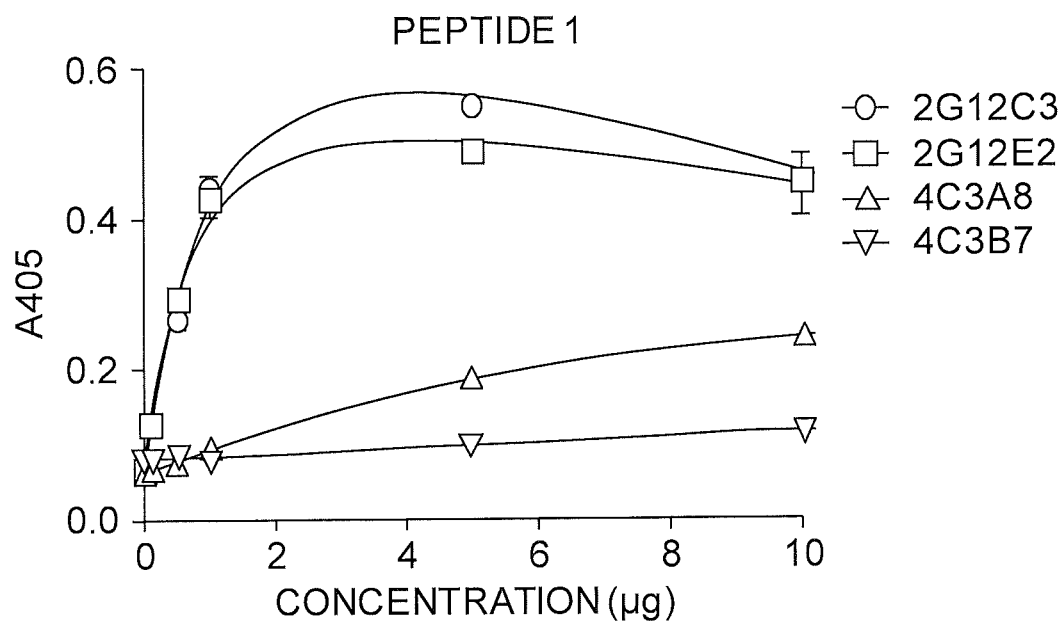

MAb 2G12C3 and 2G12E2 strongly reacted with immunogens while MAb obtained from other subclones, 4C3A8 and 4C3B7, demonstrated significantly less reactivity (FIGS. 4A and 4B).

Figure 4C:
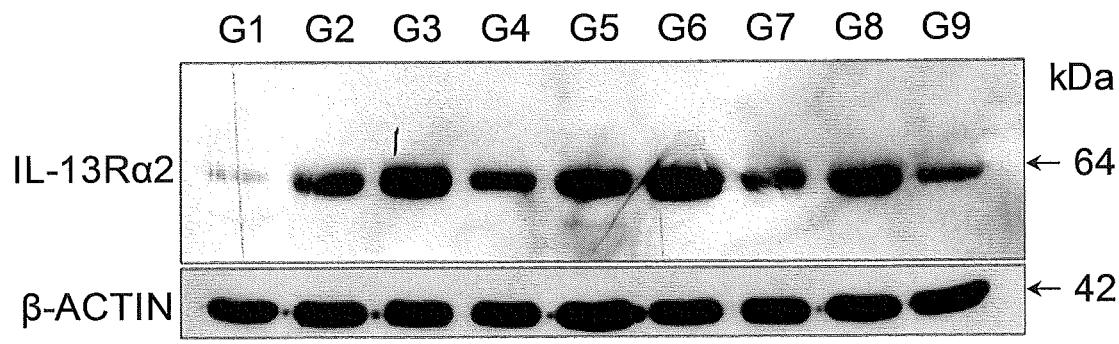
Figure 4D:
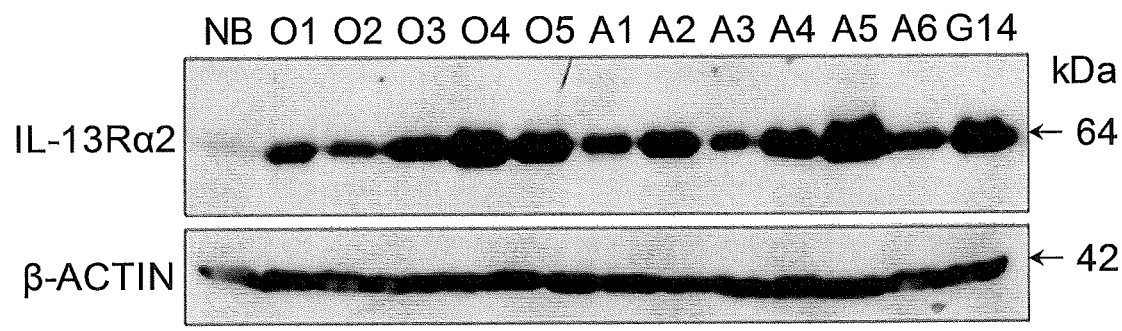
Figure 4E:
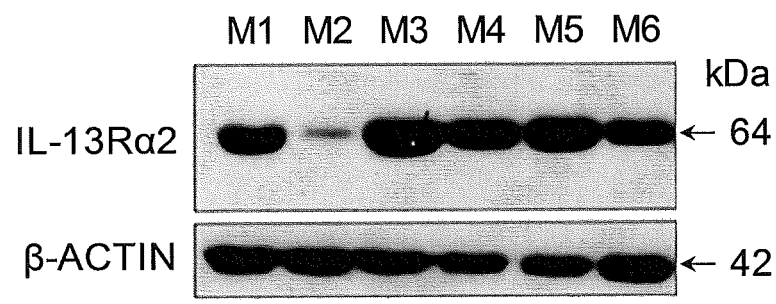

Subclone 2G12C3 was selected for further characterization. MAb 2G12C3 showed a single immunoreactive band (consistent with IL-13RA2) on western blots of cell lysates of high expressing (U-251) and low expressing (T98G) cells (FIG. 3A) comparable to previous reports (7). Western blots of tissue lysates from human brain tumors showed a single band of variable intensity in 8/9 GBMs, 5/5 oligodendrogliomas and 6/6 astrocytomas, with minimal signal in normal brain (FIGS. 4C and 4D). Five out of six meningioma tissue lysates showed strong signal, consistent with previous gene expression data (FIG. 4E) (33).

Figure 4F:
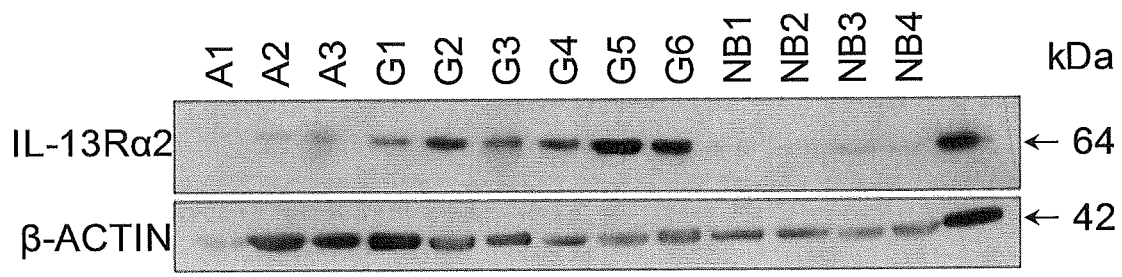
Figure 4G:
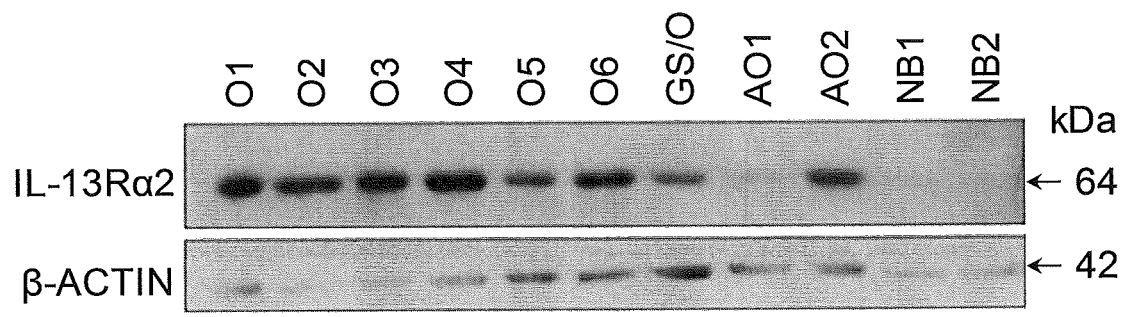
Figure 4H:
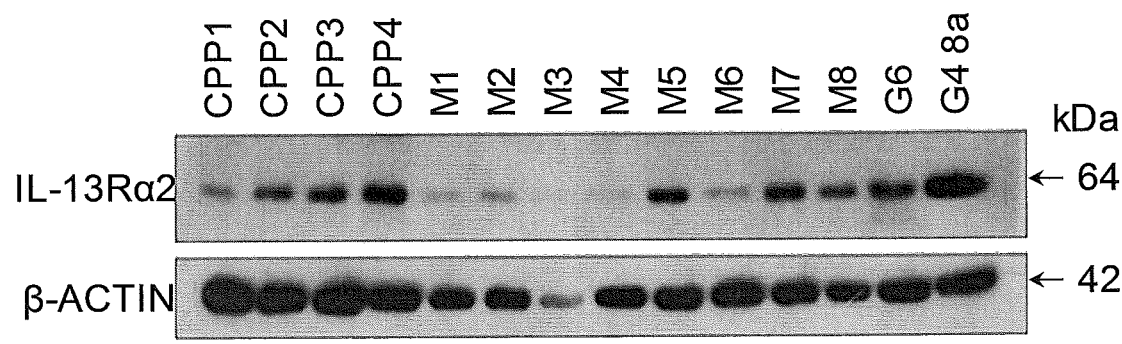

Parallel western studies were done using canine brain tumor lysates of GBM, astrocytoma (II), oligodendroglioma (III), mixed oligodendroglioma/astrocyoma, choroid plexus papilloma, meningioma and normal brain (FIGS. 4F-H). All canine GBMs (G) contained immunoreactive IL-13RA2 similarly to human specimens while canine astrocytomas (A) seem to express less of the receptor than the human tissue lysates (FIG. 4F). Oligodendrogliomas (O) expressed the receptor in a majority of samples (8/9) and at a level similar to human specimens (FIG. 3G). Interestingly, canine choroid plexus papilloma samples (CPP) (4 specimens) were noticeably enriched in IL-13RA2 (FIG. 4H). Moreover, canine meningiomas (M) expressed readily detectable receptor (6/8), but detected less than in humans (FIG. 4H).

TABLE 1

Properties of monoclonal antibodies raised against three antigenic peptides.

| Cell line | Isotype | ELISA (peptide) | ELISA (IL-13RA2-Fc) | Western Blot - Lysates | Western Blot IL-13RA2-FC | IF | IHC | Flow cytometry | Live cell binding |
|---|---|---|---|---|---|---|---|---|---|
| Peptide 1 | | | | | | | | | |
| 2G12C3 | IgG2β, κ | +* | + | + | + | − | − | − | − |
| 2G12E2 | IgG2β, κ | + | + | + | + | ND | ND | ND | ND |
| 4C3A8 | IgG2β, κ | + | + | + | + | ND | ND | ND | ND |
| 4C3B7 | IgG2β, κ | + | + | + | + | ND | ND | ND | ND |
| Peptide 2 | | | | | | | | | |
| 6D3E9 | IgM, κ | + | + | + | + | + | +/− | − | ND |
| 6D3E3 | IgM, κ | − | − | ND | − | ND | ND | ND | ND |
| 3D4E9 | IgG1, κ | +/− | − | ND | − | ND | ND | ND | ND |
| 3D4G10 | IgG1, κ | + | − | − | + | − | ND | ND | ND |
| 6F6B3 | IgG1, κ | + | + | + | + | − | ND | − | − |
| 6F6C2 | IgG1, κ | + | + | + | + | ND | ND | ND | ND |
| 4G9G3 | IgG1, κ | + | +/− | ND | +/− | − | ND | ND | ND |
| 4G9H4 | IgG1, κ | + | − | ND | − | ND | ND | ND | ND |
| Peptide 3 | | | | | | | | | |
| 1E10B9 | IgG1, κ | + | + | + | ND | + | + | + | + |
| 1E10F9 | IgG1, κ | + | + | + | ND | ND | ND | ND | ND |
| 3D11E11 | IgG1, κ | + | − | − | ND | ND | ND | ND | ND |
| 3D11H7 | IgG1, κ | + | − | − | ND | ND | ND | ND | ND |
| 5F3D7 | IgG1, κ | + | − | − | ND | ND | ND | ND | ND |
| 5F3G10 | IgG1, κ | + | − | − | ND | ND | ND | ND | ND |

* +, strongly positive; −, negative; +/−, positive; and ND, not performed

Figure 2B:
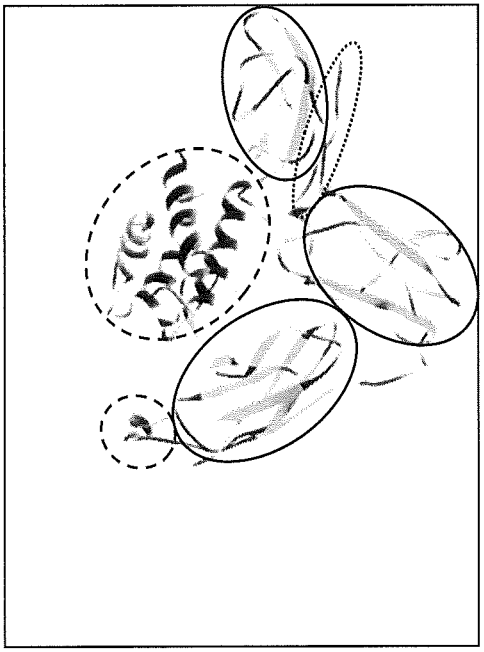
FIG. 2B. Ribbon structure of IL-13RA2 in contact with its natural ligand, IL-13. The three immunogenic peptides used for raising monoclonal antibodies are indicated. Peptide 1 is located in the extracellular domain of the receptor, Peptide 2 in the vicinity of the ligand binding to the receptor and Peptide 3 is within the transmembrane domain FIG. 3A to FIG. 3C. Immunoreactivity and purification of monoclonal antibodies induced by Peptide 1.
Figure 2B:
Figure 2B:
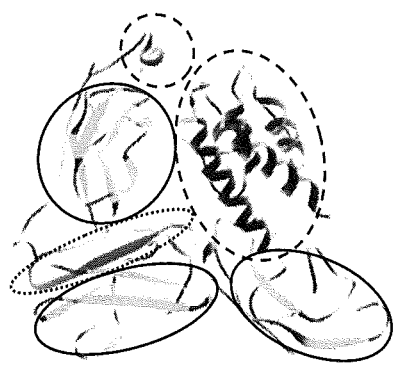

Two hybridomas with two subclones of each hybridoma (2G12C3, 2G12E2, and 4C3A8, 4C3B7) were obtained for antibodies raised against Peptide 1 (TKNL-HYKDGFDLNKGIEAKIC) (SEQ ID NO:1) (FIG. 2A) in the immunization and selection procedure. High concentrations of purified antibody were obtained from all clones (FIGS. 3B and 3C). Antibodies were assayed by ELISA using either recombinant IL-13RA2 or antigenic Peptide 1.

Normal canine brain samples either did not contain immunoreactive receptor or showed negligible amounts (FIGS. 4F and 4G).

Figure 5A:
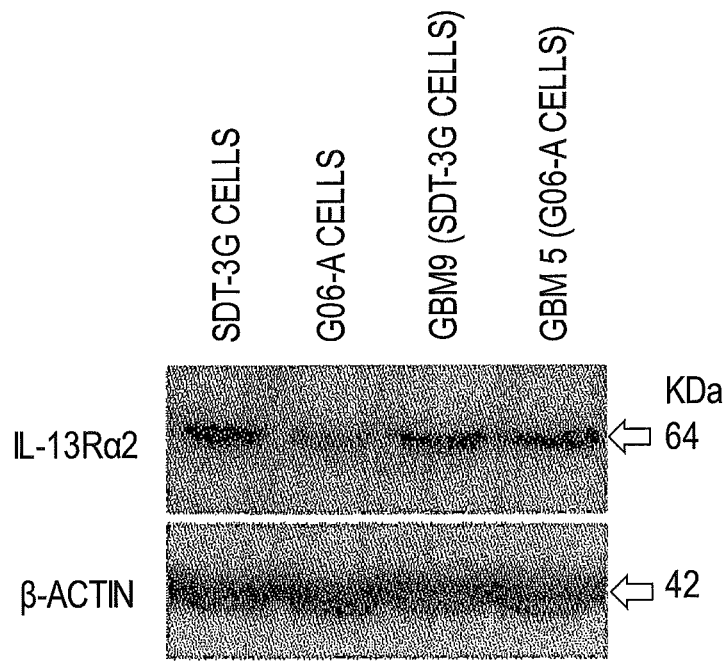
FIG. 5A to FIG. 5B. MAb 3G12C3 recognizes IL-13RA2 in both tissues and cells derived from the same specimens of canine GBM. Western blot of cell lines and parent tumor tissue obtained from dogs with spontaneous GBM, FIG. 5A. Immunoprecipitation of IL-13Rα2 from U-251 MG cell lysate using either MAb 2G12C3, MAb 2G12E2 or a polyclonal antibody (R&D Systems # AF146, FIG. 5B.
Figure 5B:
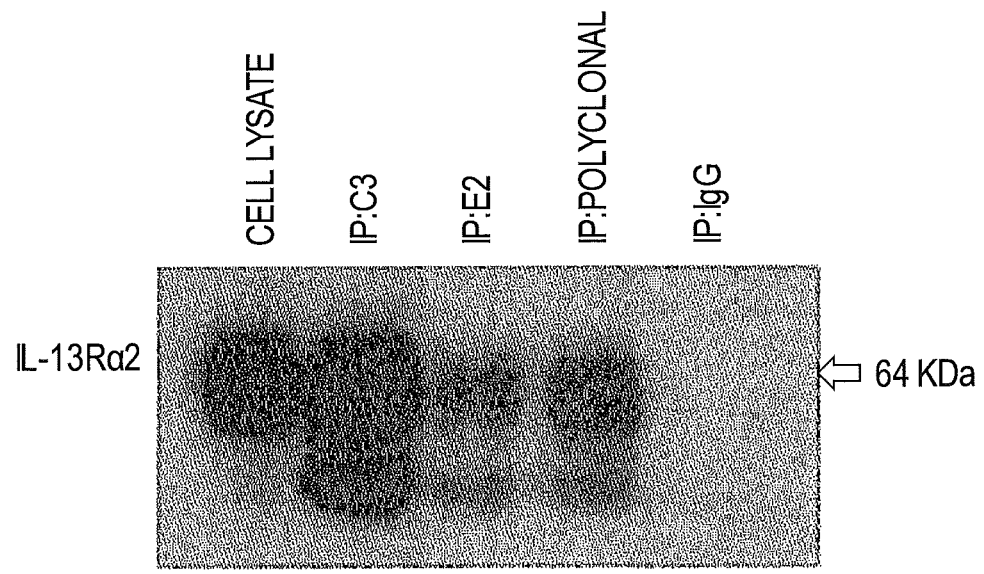

We also examined immunoreactivity of IL-13RA2 in the lysates of canine GBM cell lines, SDT-3G and G06-A cells, together with their matching tissue specimens (FIG. 5A). The expression of the receptor was detected in tissue lysates and was retained by the corresponding cells in culture.

Immunoreactive IL-13RA2 was retrieved using immunoprecipitation assays utilizing lysates of U-251 MG human established GBM cells and the 2G12C3 and 2G12E2 MAbs and a commercially available polyclonal antibody (R&D Systems # AF146). None of the MAbs raised against Peptide 1 could be successfully utilized for immunohistochemical staining or Flow Cytometry (not shown).

Figures 6E, 6F:
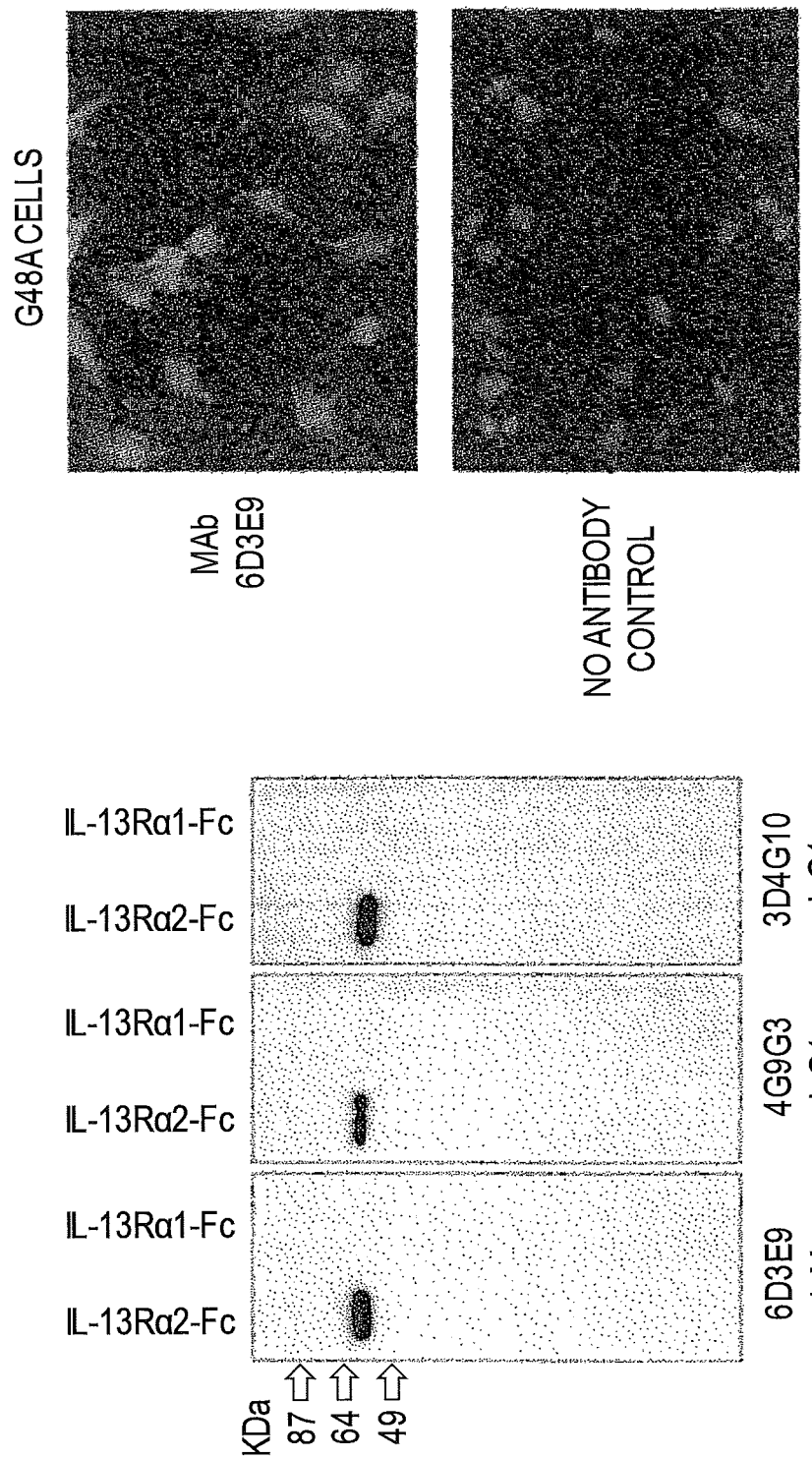

MAbs raised against Peptide 2 of homology region between human and canine IL-13RA2. Four hybridoma clones with two subclones each were obtained using Peptide 2 (SDDGIWSEWSDKQC) (SEQ ID NO: 2) as immunogen (FIG. 2A) (Table 1). Three of the clones were IgGs and one was of the IgM class (FIGS. 6A and 6B). The purified MAbs of 6F6C2, 3D4E9 and 6D3E9 reacted strongly with recombinant IL-13RA2 in ELISA; only MAb 6D3E3 did not react with the immunogenic Peptide 2 at all (FIGS. 6C and 6D). We further tested these antibodies in western blots using recombinant IL-13RA2 and IL-13RA1 as a control. 6D3E9 IgM and 4G9G3 and 3D4G10 IgG1s reacted strongly with recombinant IL-13RA2 but not with IL-13RA1 (FIG. 6E).

Some immunofluorescent staining of G48a human GBM cells (high IL-13RA2 expressors) using the IgM MAb (6D3E9) was demonstrated (FIG. 6F), Immunofluorescent staining was not obtained with any of the IgG1s of this group of MAbs, and consistent results were not obtained for any antibodies using immunohistochemical staining of formalin fixed tissue or flow cytometry (not shown).

Figure 7D:
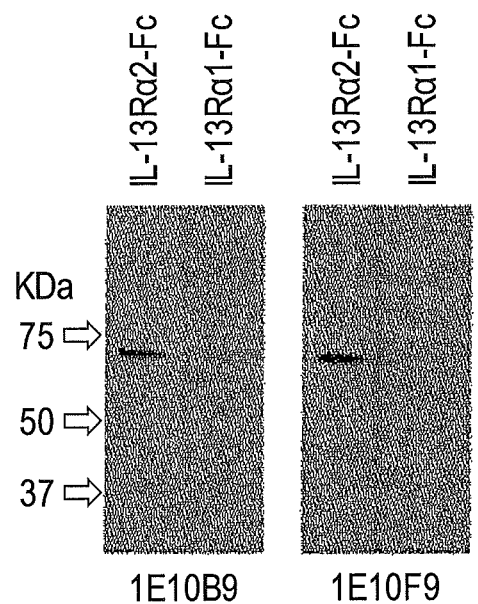
Figure 7E:
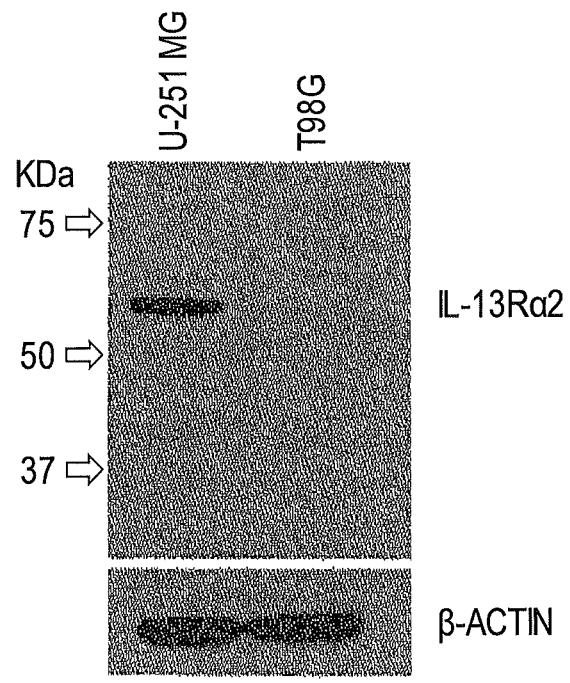
Figure 7F:
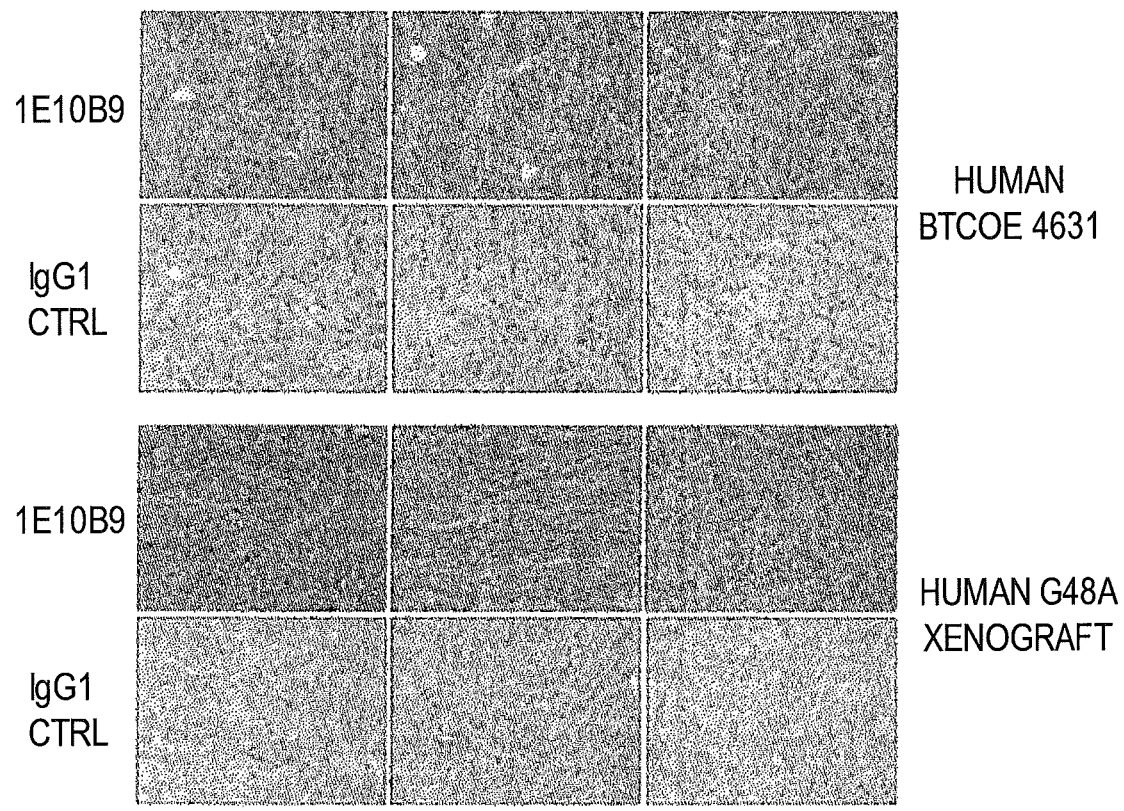
Figure 7G:
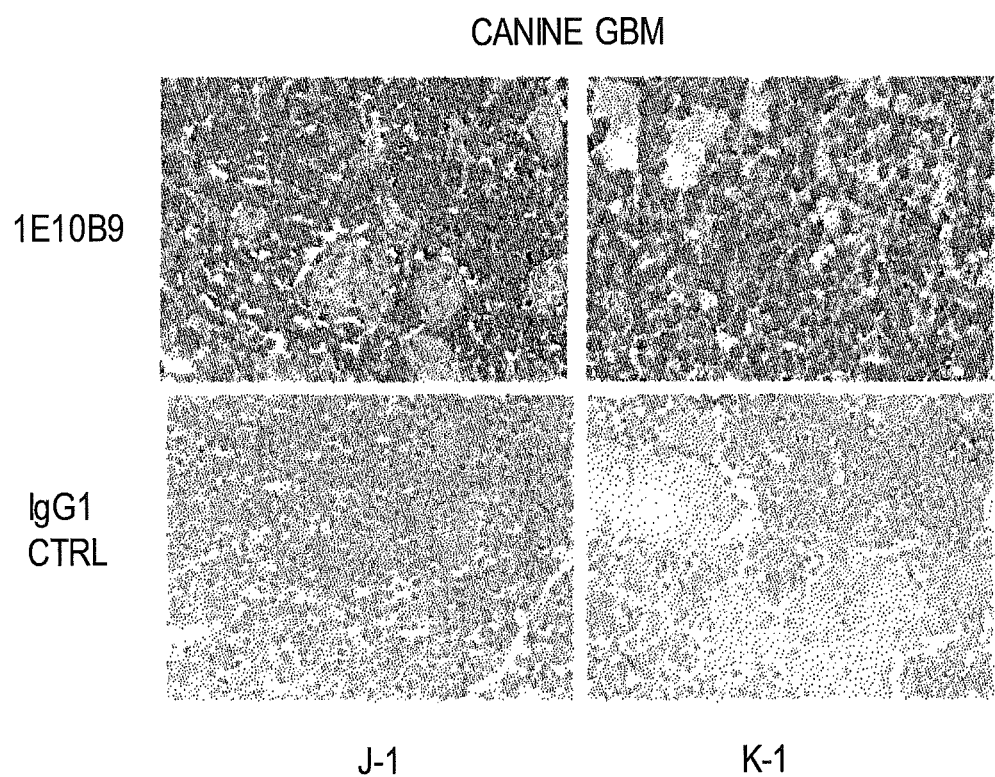
Figure 7H:
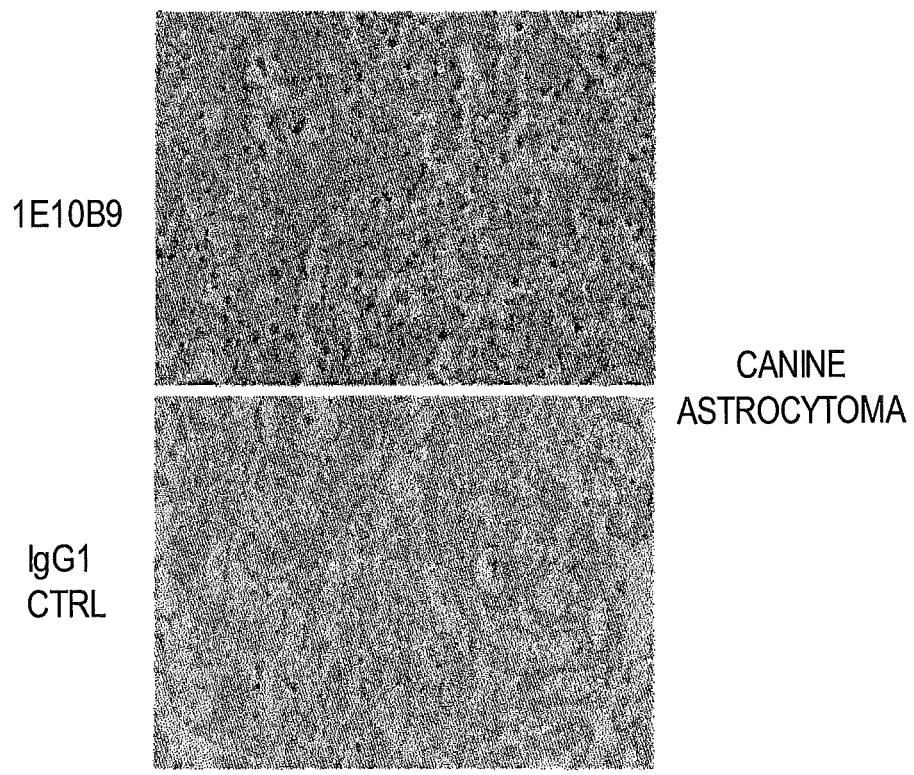
Figure 7I:
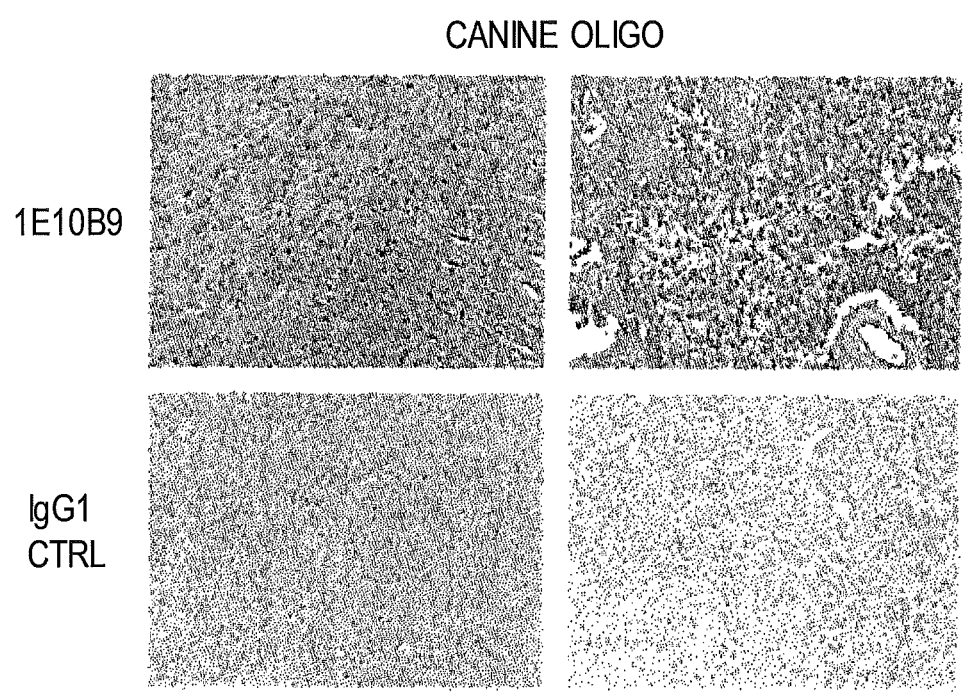
Figure 8A:
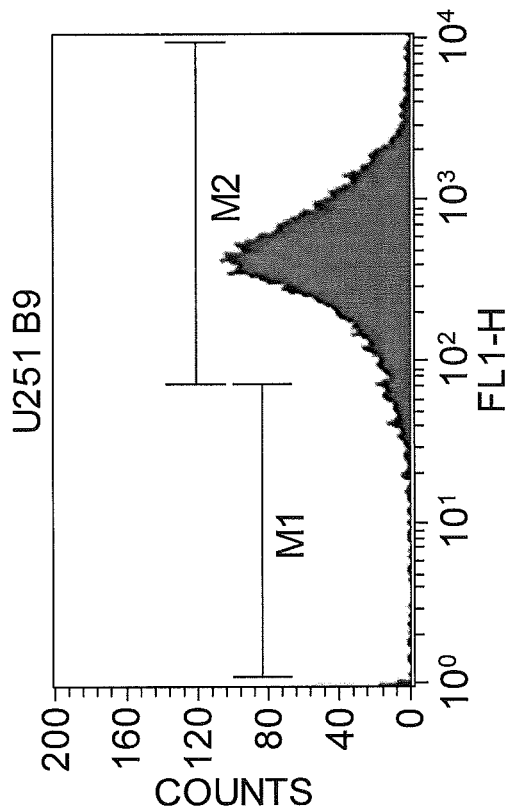
FIG. 8A to FIG. 8B. MAb 1E10B9 binds to living GBM cells. Flow cytometry on human U-251 MG cells (FIG. 8A) and canine GBM G06-A cells (FIG. 8B) using MAb 1E10B9.
Figure 8A:
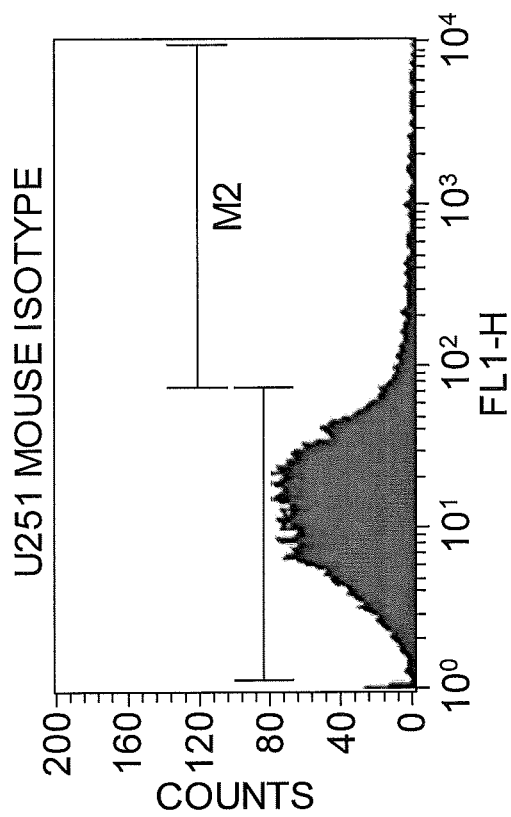
Figure 8A:
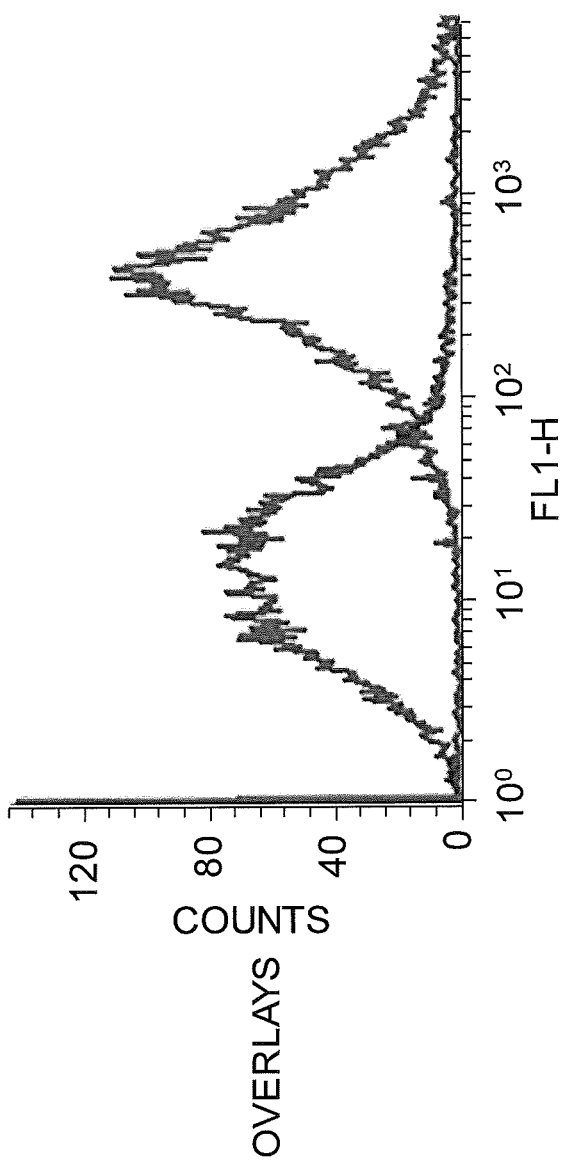
Figure 8B:
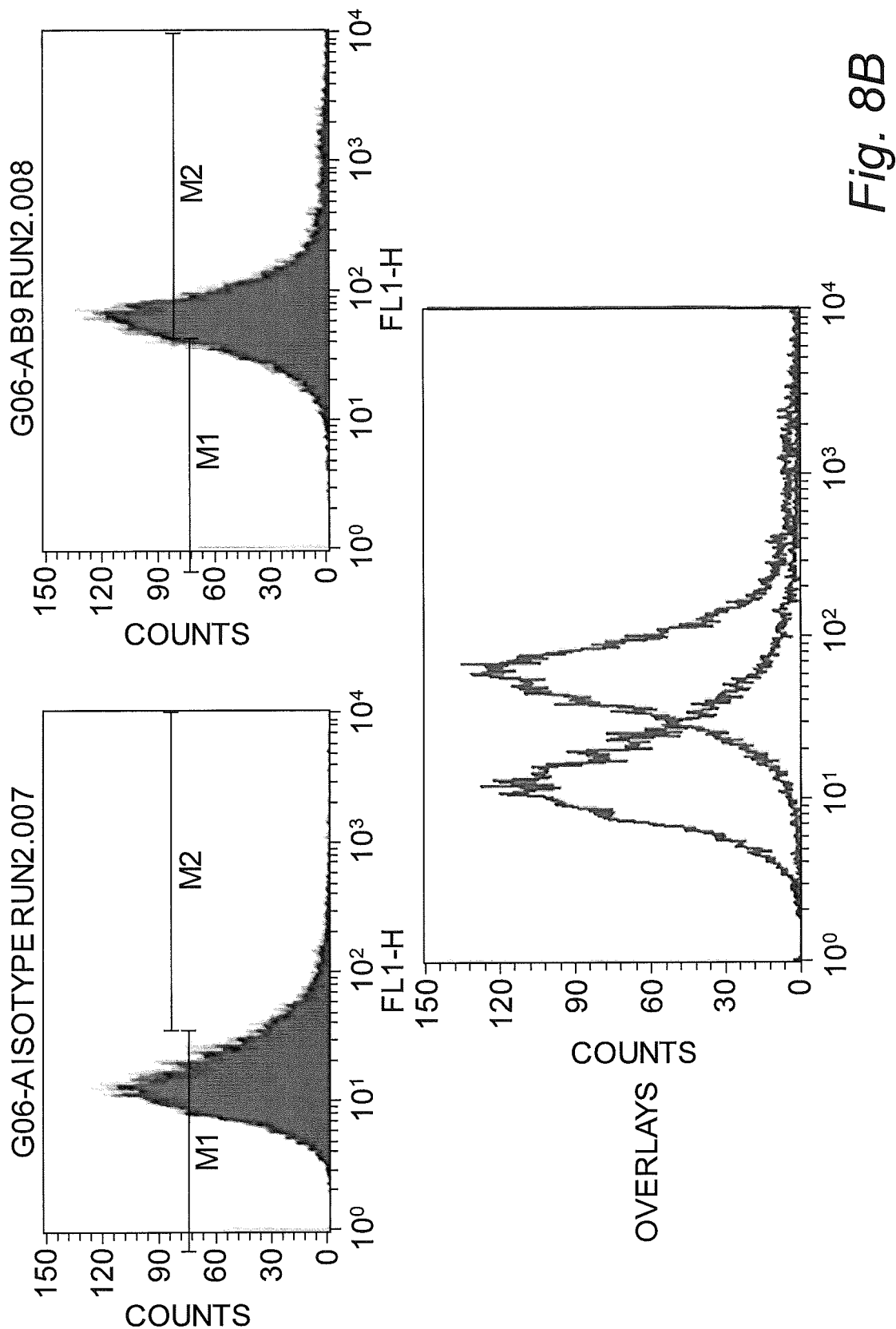

MAbs raised against Peptide 3 of homology region between human and canine IL-13RA2. In the last immunization protocol using Peptide 3 (SDYKDFYICVNGSSE) (SEQ ID NO: 3) (FIG. 2A) three hybridoma subclones were obtained with two subclones each (Table 1). The MAbs were purified from the media (FIG. 7A; MAb 1E10B9 is depicted) and demonstrated variable reactivity by ELISA using either recombinant receptor or immunogenic Peptide 3 (FIGS. 7B and 7C). Two IgG MAbs, 1E10B9 and 1E10F9 reacted most positively in these assays and they were further characterized in additional experiments. In western blots with recombinant IL-13RA2 and IL-13RA1, these antibodies reacted only with the tumor-associated receptor, IL-13RA2 (FIG. 7D). MAb 1E10B9 also detected an immunoreactive band of IL-13RA2 in U-251 MG and T89 cells, similar to Peptide 1 clone 2G12C3 (FIG. 7E). We next performed immunohistochemistry on human and canine tumor specimens as well as on sectioned human xenografts growing in immunocompromised animals. MAb 1E10B9 demonstrated strong staining in human tissue specimens of GBM, G48a human GBM xenograft tumors (FIG. 7F), canine GBMs, (FIG. 7G) astrocytomas (FIG. 7H) and oligodendrogliomas (FIG. 7I). Additionally, MAb 1E10B9 using flow cytometry on human U-251 MG cells (FIG. 8A) and canine G06-A cells (FIG. 8B) and found robust binding of the antibody to the receptor present on the surface of live cells. Thus, MAb 1E10B9 recognizes IL-13RA2 in ELISA, western blot and immunohistochemistry assays, and binds to live cells expressing the receptor.

Canine IL-13 Based Cytotoxins Kill GBM Cells in a Targeted Manner.

Figure 9A:
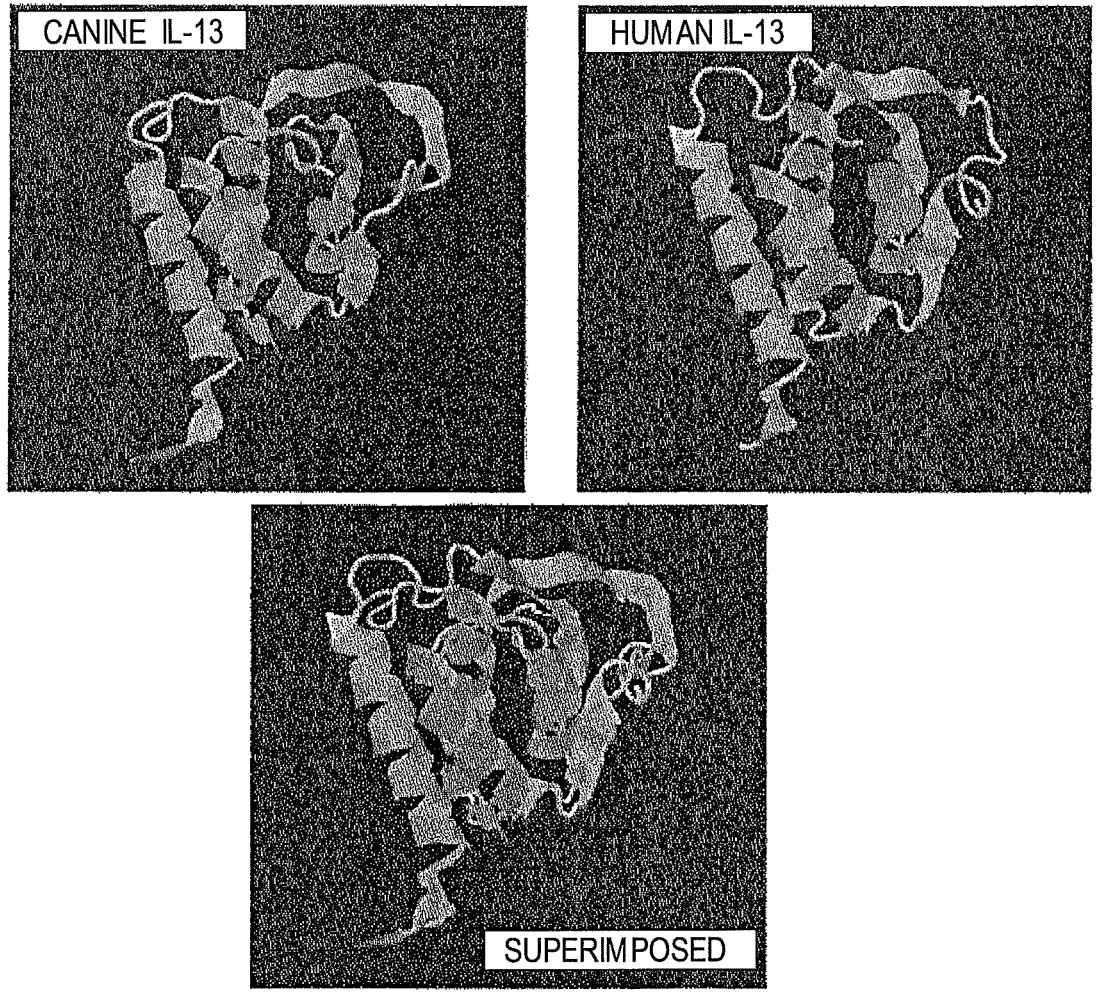
Figure 9C:
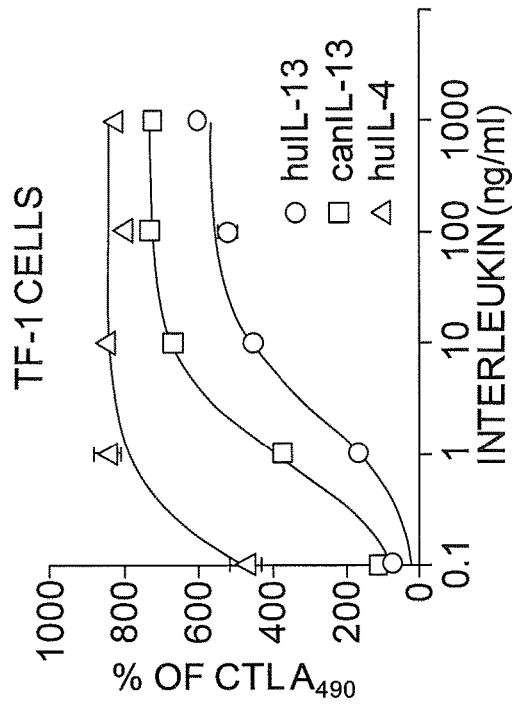
Figure 9E:
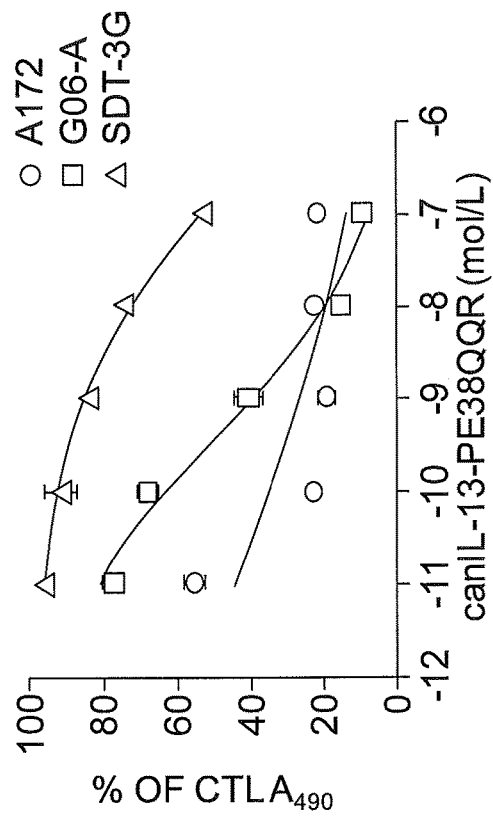
Figure 9B:
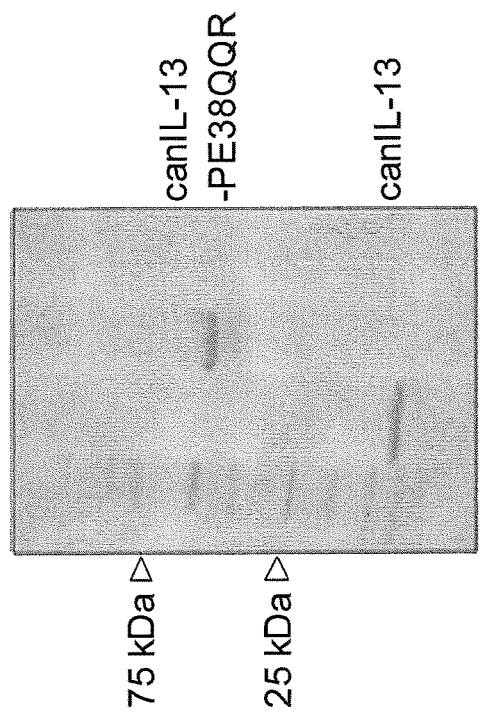
Figure 9D:
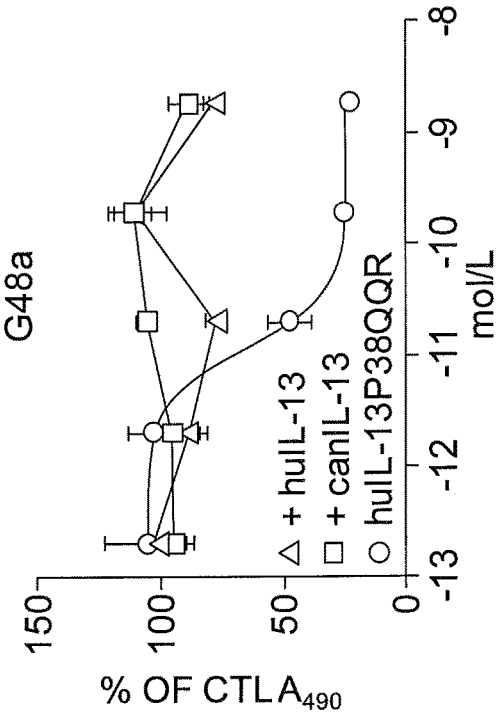

Human and canine IL-13 have very similar 3-D structure as seen in FIG. 9A, but there are clear variances in spatial arrangements of these molecules most likely related to the fit of the ligands to their species-relevant receptors. Previous studies (not shown) determined that human IL-13 (huIL-13) conjugated toxins did not result in efficient targeted killing of canine glioma cell lines in vitro. Therefore, we cloned and produced highly purified recombinant canine IL-13 (canIL-13) and a single-chain cytotoxin containing canIL-13 and a derivative of Pseudomonas exotoxin A (PE), PE38QQR (FIG. 9B). Functionality of canIL-13 was determined by assessing induction of proliferation in human-derived TF-1 cells that express the IL-4RA/IL-13RA1 physiological receptor for IL-13. CanIL-13 was more potent than huIL-13 while maximal proliferation was seen using hIL-4 (FIG. 9C). Thus our recombinant canIL-13 demonstrates biological activity comparable to the human IL-13 cytokine. Next, we tested the ability of canIL-13 to neutralize the cytotoxic action of huIL-13-PE38QQR on human G48a GBM cells that over-express IL-13RA2. CanIL-13 blocked the killing effect of the cytotoxin similarly to huIL-13 (FIG. 9D) indicating an efficient competition of canIL-13 for human IL-13RA2.

We next tested the recombinant canIL-13-PE38QQR cytotoxin on both human and canine GBM cell lines. CanIL-13-PE38QQR was potent in killing both canine (SDT-3G, G06-A) and human (A-172) GBM cells (FIG. 9E). CanIL-13 cytotoxin action was blocked by both canIL-13 and huIL-13 on low passage human GBM cells (BTCOE 4795) and canine G06-A GBM cells (FIG. 9F-G).

Sequence data for MAb 1E10B9 is provided below:

```
Variable light chain DNA sequence
(Amino acids upstream were from the protein
sequencing data)
                                      (SEQ ID NO: 7)
CCA CTC ATT TTG TCA GTT ACC ATT GGA CAA CCA GCC

TCT ATC TCT TGC AAG TCA AGT CAG AGC GTC TTA TAT

AGT AAT GGA AAA ACC TAT TTG AAT TGG TTA TTA CAG

AGG CCA GGC CAG TCT CCA AAG CGC CTA ATC TAT CTG

GTG TCT AAA CTG GAC TCT GGA GTC CCT GAC AGG TTC

ACT GGC AGT GGA TCA GGA ACA GAT TTT ACA TTG AAA

ATC AGC AGA GTG GAG GCT GAA GAT TTG GGA GTT TAT

TAC TGC GTG CAA GGT TCA CAT TTT CCG TAC ACG TTC

GGA GGG GGG ACC AAG CTG GAA ATA AAA CGG GCT GAT

GCT

Variable light chain protein sequence
                                      (SEQ ID NO: 8)
E I V M T Q T P L I L S V T I G Q P A S I S C K

S S Q S V L Y S N G K T Y L N W L L Q R P G Q S

P K R L I Y L V S K L D S G V P D R F T G S G S

G T D F T L K I S R V E A E D L G V Y Y C V Q G

S H F P Y T F G G G T K L E I K R A D A

Variable heavy chain DNA
                                      (SEQ ID NO: 9)
GGA CCT GAG CTG AAG AAG CCT GGA GAG ACA GTC AAG

ATC TAC TGC AAG GCT TCT GGT TAT TCC TTC AGA GAC

TAT TCA GTG CAC TGG GTG AAA CAG GCT CCA GGA AAG

GGT TTA AAG TGG ATG GGC TGG ATA AAT ACT GAG ACT

GGT GAA CCA ACA TAT GTG GAT GAA TTC AAG GGA CGA

TTT GCC TTC TTT TTG GAA GCC TCT GCC AAC ACT GTC

TAT TTG CAG ATC AGC AAC CTC AAA AAT GAG GAC ACG
```

```
-continued
GCT ACA TAT TTC TGT GAC TAC CGT TTT ACT TAC TGG

GGC CAG GGG ACT CTG GTC ACT GTC TCT GCA GCC AAA

Variable heavy chain protein sequence
                                         (SEQ ID NO: 10)
G P E L K K P G E T V K I Y C K A S G Y S F R D

Y S V H W V K Q A P G K G L K W M G W I N T E T

G E P T Y V D E F K G R F A F F L E A S A N T V

Y L Q I S N L K N E D T A T Y F C D Y R F T Y W

G Q G T L V T V S A A K
```

Discussion

We have generated a panel of monoclonal antibodies against IL-13RA2, a tumor-associated receptor, that are suitable for pharmaceutical targeting (Table 1). These antibodies cross-react with the homologous canine receptor and thus may be used in this species in translational studies. Three various regions of the receptor targeting either extracellular, or ligand-binding domains with 100% of homology between human and canine receptors were chosen for the production of immunogenic peptides, Peptides 1-3 from different regions of the receptor. Most purified antibodies reacted with the immunogenic peptides and recombinant receptor in vitro. Also most antibodies were useful in the detection of immunoreactive IL-13RA2 in cell and tissue lysates using western blotting with no cross-reactivity for the closely related IL-13RA1. One antibody raised against Peptide 3 (MAb 1E10B9) was found to efficiently bind live cells and work well in immunohistochemical staining. Our novel antibodies (Table 1) detected IL-13RA2 in a variety of human and canine brain tumors and cell lines on western blots, defining an extended spectrum of potential target tumors beyond the high grade astrocytomas previously reported (3,19). Importantly, absence or negligible expression of the target was confirmed in both human and canine normal brain.

The presence of the receptor in various tumors other than human and canine GBM tumors differed. For example, human astrocytomas, oligodendrogliomas and meningiomas demonstrated high levels of IL-13RA2 immunoreactivity. While canine oligodendrogliomas showed similarly high presence of the receptor protein, meningiomas were less enriched in the receptor comparatively to human samples. Interestingly, canine choroid-plexus tumors contained high amounts of immunoreactive IL-13RA2; human choroid plexus tumors were not investigated in the current study.

One of the isolated antibodies, MAb 1E10B9, demonstrated a number of attractive features. It recognized IL-13RA2 in cell and tumor lysates using western blot and resulted in robust immunohistochemical staining in archival paraffin embedded specimens. Importantly, it bound live GBM cells of both human and canine origin. This versatility offers multiple potential applications for MAb 1E10B9 for diagnostic, imaging and therapeutic approaches.

IL-13RA2 is an attractive molecular target in a variety of human malignancies and in primary brain tumors in particular. The current study demonstrates that it is also a valid target in a clinically relevant spontaneous animal model of human disease, namely spontaneously occurring canine brain tumors. The IL-13RA2 receptor belongs to a tri-molecular signature of human GBM also including the EphA2 receptor and a transcription factor Fra-1 (19), and recent studies are suggestive of IL-13RA2 belonging to a group of factors characterizing glioma stem-like cells (36, 37). The availability of specific and sensitive antibodies recognizing the receptor under various conditions will be important in further studies examining the pathophysiological role of IL-13RA2 in brain tumors, including its closest translational model in a form of spontaneous canine tumors.

Validation of IL-13RA2 as a target in canine brain tumors and generation of a novel canIL-13 based cytotoxin demonstrating potent and specific killing of canine GBM cells will allow for validation and development of IL-13RA2 targeted therapeutic strategies in a clinically relevant translational model system. It is hoped that use of this approach will help bridge the gap between in vitro and rodent based proof of principal experiments and the clinical arena. Previously, the first generation of IL-13 cytotoxin prolonged significantly the survival of patients with recurrent GBM when used in centers experienced with loco-regional deliveries drugs (38), but imaging was not employed and thus drug delivery was not standardized among all centers. Based on the observations presented here, a Phase I clinical trial in the treatment of canine astrocytomas has begun utilizing IL-13Rα2- and EphA 2-(19) targeted cytotoxins in combination. This trial involves using dogs/real time imaging to define appropriate delivery of the targeted therapy to the "target" (28).

REFERENCES

1. Stupp R, Mason W P, van den Bent M J, et al. (2005) Radiotherapy plus concomitant and adjuvant temozolomide for glioblastoma. N Engl J Med 352: 987-996.
2. Debinski W, Obiri N I, Powers S K, Pastan I, and Puri R K (1995) Human glioma cells overexpress receptor for interleukin 13 and are extremely sensitive to a novel chimeric protein composed of interleukin 13 and Pseudomonas exotoxin. Clin Cancer Res 1: 1253-1258.
3. Debinski W, Gibo D M, Hulet S W, Connor J R, and Gillespie G Y (1999) Receptor for interleukin 13 is a marker and therapeutic target for human high grade gliomas. Clin Cancer Res 5: 985-990.
4. Mintz A, Gibo D M, Webb (Slagle) B, and Debinski W (2002) IL13Rα2 is a glioma-restricted receptor for IL13. Neoplasia 4: 388-399.
5. Debinski W (1998) An immune regulatory cytokine receptor and glioblastoma multiforme: an unexpected link. Crit Rev Oncog 9: 255-268.
6. Debinski W, and Gibo D M (2000) Molecular expression analysis of restrictive receptor for interleukin 13, a brain tumor-associated cancer/testis antigen. Mol Med 6: 440-449.
7. Hu N, Gibo D M, and Debinski W (2005) Cytokine up-regulation of IL-13Rα2 in GBM cells leads to an increased potency of recombinant IL13 cytotoxin. Cancer Therapy 3: 531-542.
8. Lal A, Glazer C A, Martinson H M et al. (2002) Mutant epidermal growth factor receptor up-regulates molecular effectors of tumor invasion. Cancer Res 62: 3335-3339.
9. Mintz A, and Debinski W (2000) Cancer genetics/epigenetics and the X chromosome: Possible new links for malignant glioma pathogenesis and immune-based therapies. Critic Rev Oncogen 11: 77-95.
10. Okano F, Storkus W J, Chambers W H, Pollack I F, and Okada H (2002) Identification of a novel HLA-A*0201-restricted, cytotoxic T lymphocyte epitope in a human glioma-associated antigen, interleukin 13 receptor α2 chain. Clin Cancer Res 8: 2851-2855.
11. Mintz A, Gibo D M, Madhankumar A B, Cladel N M, Christensen N D, Debinski W (2008) Protein and DNA-based active immunotherapy targeting interleukin 13 receptor alpha 2. Cancer Biother and Radiopharm 23: 581-589.
12. Zhou G, Ye G-J, Debinski W, and Roizman B (2002) Genetic engineering of a herpes virus 1 vector dependent on the IL-13Rα2 receptor for entry into cells: interaction of glycoprotein D with its receptors is independent of the fusion of the envelope and the plasma membrane. Proc Natl Acad Sci 99: 15124-15129.
13. Kahlon K S, Brown C, Cooper L J N, Raubitschek A, Forman S J, and, Jensen M C. 2004. Specific recognition and killing of glioblastoma multiforme by interleukin 13-zetakine redirected cytolytic T cells. Cancer Res 64:9160-9167.
14. Chunbin L, Hall W A, Jin N, Todhunter D A, Panoskaltis-Mortari A, and Vallera D A (2002) Targeting glioblastoma multiforme with an IL-13/diphtheria toxin fusion protein in vitro and in vivo in nude mice. Prot Engin 15: 419-427.
15. Debinski W, Gibo D M, Kealiher A, and Puri R K (1998) Novel anti-brain tumor cytotoxins specific for cancer cells. Nature Biotech 16: 449-453.
16. Mintz A, Gibo D M, Madhankumar A B, and Debinski W (2003) Molecular targeting with recombinant cytotoxins of interleukin-13 receptor alpha-2-expressing glioma. J Neuro-Oncol 64: 117-123.
17. Ulasov I V, Tyler M A, Han Y, Glasgow J N, Lesniak M S (2007) Novel recombinant adenoviral vector that targets the interleukin-13 receptor alpha2 chain permits effective gene transfer to malignant glioma. Hum Gene Ther 18: 118-129.
18. Candolfi M, Xiong W, Yagiz K, Liu C, Muhammad A K, et al. (2010) Gene therapy-mediated delivery of targeted cytotoxins for glioma therapeutics. Proc Natl Acad Sci 107: 20021-20026.
19. Wykosky J, Gibo D M, Stanton C, Debinski W (2008) IL-13 Receptor alpha-2, EphA2, and Fra-1 as molecular denominators of high-grade astrocytomas and specific targets for combinatorial therapy. Clin. Cancer Res 14: 199-208.
20. Fankhauser R, Luginbühl H, McGrath J T (1974) Tumours of the nervous system. Bull World Health Organ 50: 53-69.
21. Priester W A, Mantel N (1971) (Occurrence of tumors in domestic animals. Data from 12 United States and Canadian colleges of veterinary medicine. J Natl Cancer Inst 47: 1333-1344.
22. Schneider R (1978) General considerations, in: Tumors in Domestic Animals, University of California Press, Berkley, 2nd Ed, Ed Moulton, J E, pg 1-5.
23. Priester W A, McKay F W (1980) The occurrence of tumors in domestic animals, Ed Ziegler J L, National Cancer Institute Monograph, US Dept of Health and Human Services, Bethesda, Md. Pg 1-210.
24. Hayes H M, Priester W A Jr, Pendergrass T W (1975) Occurrence of nervous-tissue tumors in cattle, horses, cats and dogs. Int J Cancer 15: 39-47.
25. Luginbuhl, H, Fankhauser, R, McGrath, J T (1968) "Spontaneous neoplasms of the nervous system of animals," Prog Neurology Surgery 2: 85-164,
26. Rossmeisl Jr. J H, Jones J C, Zimmerman K L, et al. (2013) Survival time following hospital discharge in dogs with palliatively treated primary brain tumors. J Am Vet Med Assoc 242: 193-198.
27. Candolfi M, Curtin J F, Nichols W S, Muhammad A G, King G D et al. Intracranial glioblastoma models in preclinical neuro-oncology: neuropathological characterization and tumor progression. J Neurooncol. 85: 133-148. (2007)
28. Dickinson P J, LeCouteur R A, Higgins R J, Bringas J R, Roberts B et al. (2008) Canine model of convection-enhanced delivery of liposomes containing CPT-11 monitored with real-time magnetic resonance imaging: laboratory investigation. J Neurosurg 108: 989-998.
29. Dickinson P J, LeCouteur R A, Higgins R J, Bringas J R, Larson R F et al. (2010) Canine spontaneous glioma: a translational model system for convection-enhanced delivery. Neuro Oncol 12: 928-940.
30. Pluhar G E, Grogan P T, Seiler C, Goulart M, Santacruz K S et al. (2010) Anti-tumor immune response correlates with neurological symptoms in a dog with spontaneous astrocytoma treated by gene and vaccine therapy. Vaccine 28: 3371-3378.
31. Louis D N, Ohgaki H, Wiestler O D, Cavenee W K, Burger P C et al. (2007) The 2007 WHO classification of tumours of the central nervous system. Acta Neuropathol 114: 97-109.
32. Debinski W, Gibo D M (2005) Fos-related antigen 1 modulates malignant features of glioma cells. Mol Cancer Res 3: 237-249.
33. Dickinson P J, Roberts B N, Higgins R J, Leutenegger C M, Bollen A W et al. (2006) Expression of receptor tyrosine kinases VEGFR-1 (FLT-1), VEGFR-2 (KDR), EGFR-1, PDGFRalpha and c-Met in canine primary brain tumours. Vet Comp Oncol. 4: 132-140.
34. Debinski W, Obiri N I, Pastan I, Puri R K (1995) A novel chimeric protein composed of interleukin 13 and *Pseudomonas* exotoxin is highly cytotoxic to human carcinoma cells expressing receptors for interleukin 13 and interleukin 4. J Biol Chem 270: 16775-16780.
35. Joshi B H, Plautz G E, Puri R K (2000) Interleukin-13 receptor alpha chain: a novel tumor-associated transmembrane protein in primary explants of human malignant gliomas. Cancer Res 60: 1168-1172.
36. Nguyen V, Conyers J M, Zhu D, Gibo D M, Dorsey J F et al. (2011) IL-13Rα2-Targeted Therapy Escapees: Biologic and Therapeutic Implications. Transl Oncol 4: 390-400.
37. Brown C E, Starr R, Aguilar B, Shami A F, Martinez C et al. (2012) Stem-like tumor-initiating cells isolated from IL-13Rα2 expressing gliomas are targeted and killed by IL13-zetakine-redirected T Cells. Clin Cancer Res 18: 2199-2209.
38. Sampson J H, Archer G, Pedain C, Wembacher-Schröder E, Westphal M et al. (2010) Poor drug distribution as a possible explanation for the results of the PRECISE trial. J Neurosurg 113: 301-309.

The foregoing is illustrative of the present invention, and is not to be construed as limiting thereof. The invention is defined by the following claims, with equivalents of the claims to be included therein.

What is claimed is:

1. A method of treating a tumor in a subject in need thereof comprising administering to said subject in a treatment effective amount an antibody that specifically binds an epitope within amino acids spanning the extracellular portion of human IL-13RA2, wherein said epitope is within amino acids spanning the extracellular portion of human IL-13RA2 that have at least 90% identity with the corresponding canine sequence of IL-13RA2, and wherein said antibody is coupled to a chemotherapeutic agent,
wherein said epitope is within amino acids of SEQ ID NO: 1 (Peptide 1); SEQ ID NO: 2 (Peptide 2); or SEQ ID NO: 3 (Peptide 3),
wherein said antibody comprises a variable light chain amino acid sequence of SEQ ID NO:8 or at least 95% identity thereto, and a variable heavy chain amino acid sequence of SEQ ID NO:10 or at least 95% identity thereto, and
wherein said antibody specifically binds to both human and canine IL-13RA.

2. The method of claim 1, wherein said tumor comprises cells having elevated IL-13RA2 expression as compared to the corresponding non-cancerous cells.

3. The method of claim 1, wherein said tumor is a brain tumor.

4. The method of claim 3, wherein said brain tumor is an astrocytoma, meningioma or oligodendroglioma.

5. The method of claim 3, wherein said brain tumor is glioblastoma multiforme (GBM).

6. The method of claim 3, wherein said antibody is administered to said subject by intra-cerebral administration.

7. The method of claim 3, wherein said antibody is administered by intracerebroventricular infusion.

8. The method of claim 3, wherein said antibody is administered by intrathecal infusion.

9. The method of claim 3, wherein said antibody is administered into the brain of said subject by convection-enhanced delivery (CED).

10. The method of claim 1, wherein said tumor is breast cancer, ovarian cancer, kidney cancer, bladder cancer, pancreatic cancer, gastric cancer, colorectal cancer, head and neck cancer, thyroid cancer, prostate cancer, or Kaposi's sarcoma.

11. The method of claim 1, wherein said antibody is administered as a liposomal formulation.

12. The method of claim 1, wherein said subject is a human subject.

13. The method of claim 1, wherein said subject is a human subject at least 60, 65 or 70 years old.

14. The method of claim 1, wherein said subject is a canine subject.

15. The method of claim 1, wherein said antibody is administered in an amount of from about 0.01 to about 400 mg/kg.

16. The method of claim 1, wherein said antibody is administered by continuous infusion over a period of from about 7 to about 14 days.

17. The method of claim 1, wherein said epitope comprises at least 4 consecutive amino acids from SEQ ID NO:1, SEQ ID NO:2, or SEQ ID NO:3.

18. The method of claim 1, wherein said chemotherapeutic agent is a bacterial toxin or derivative thereof.

19. A method of inhibiting cancer metastasis in a subject in need thereof comprising administering to said subject in a treatment effective amount an antibody that specifically binds an epitope within amino acids spanning the extracellular portion of human IL-13RA2, wherein said epitope is within amino acids spanning the extracellular portion of human IL-13RA2 that have at least 90% identity with the corresponding canine sequence of IL-13RA2, and wherein said antibody is coupled to a chemotherapeutic agent,
wherein said epitope is within amino acids of SEQ ID NO: 1 (Peptide 1); SEQ ID NO: 2 (Peptide 2); or SEQ ID NO: 3 (Peptide 3),
wherein said antibody comprises a variable light chain amino acid sequence of SEQ ID NO:8 or at least 95% identity thereto, and a variable heavy chain amino acid sequence of SEQ ID NO:10 or at least 95% identity thereto, and wherein said antibody specifically binds to both human and canine IL-13RA.

20. The method of claim 19, wherein said cancer comprises cells having elevated IL-13RA2 expression as compared to the corresponding non-cancerous cells.

21. The method of claim 19, wherein said cancer is a brain cancer.

22. The method of claim 21, wherein said brain cancer is an astrocytoma, meningioma or oligodendroglioma.

23. The method of claim 21, wherein said brain cancer is glioblastoma multiforme (GBM).

24. The method of claim 19, wherein said cancer is breast cancer, ovarian cancer, kidney cancer, bladder cancer, pancreatic cancer, gastric cancer, colorectal cancer, head and neck cancer, thyroid cancer, prostate cancer, or Kaposi's sarcoma.

25. The method of claim 19, wherein said subject is a human subject.

26. The method of claim 19, wherein said subject is a canine subject.

27. The method of claim 19, wherein said antibody is administered in an amount of from about 0.01 to about 400 mg/kg.

28. The method of claim 19, wherein said antibody is administered by continuous infusion over a period of from about 7 to about 14 days.

29. The method of claim 19, wherein said epitope comprises at least 4 consecutive amino acids from SEQ ID NO:1, SEQ ID NO:2, or SEQ ID NO:3.

30. The method of claim 19, wherein said chemotherapeutic agent is a bacterial toxin or derivative thereof.

* * * * *

UNITED STATES PATENT AND TRADEMARK OFFICE
CERTIFICATE OF CORRECTION

PATENT NO. : 10,676,529 B2
APPLICATION NO. : 15/835566
DATED : June 9, 2020
INVENTOR(S) : Debinski et al.

Page 1 of 1

It is certified that error appears in the above-identified patent and that said Letters Patent is hereby corrected as shown below:

On the Title Page

Item (56) References Cited, OTHER PUBLICATIONS, Page 2, Column 1, Line 25, Fujisawa T et al. cite: Please correct "Jul. 16, 2012" to read -- Jul. 15, 2012 --

Item (56) References Cited, OTHER PUBLICATIONS, Page 2, Column 2, Line 13, GenBank Accession cite: Please correct "Jun. 30, 2015" to read -- Jun. 30, 2016 --

In the Specification

Column 18, Line 59: Please correct "P<0.05" to read -- $P \leq 0.05$ --

Signed and Sealed this
Twenty-seventh Day of October, 2020

Andrei Iancu
*Director of the United States Patent and Trademark Office*